(12) United States Patent
Taylor

(10) Patent No.: US 7,201,063 B2
(45) Date of Patent: Apr. 10, 2007

(54) NORMAL FORCE GRADIENT/SHEAR FORCE SENSORS AND METHOD OF MEASURING INTERNAL BIOLOGICAL TISSUE STRESS

(76) Inventor: Geoffrey L. Taylor, 211 Oak Street, Winnipeg, Manitoba (CA) R3M 3P7

( * ) Notice: Subject to any disclaimer, the term of this patent is extended or adjusted under 35 U.S.C. 154(b) by 189 days.

(21) Appl. No.: 10/836,495

(22) Filed: Apr. 30, 2004

(65) Prior Publication Data

US 2005/0241409 A1    Nov. 3, 2005

(51) Int. Cl.
*G01N 3/24* (2006.01)
*G01N 3/04* (2006.01)

(52) U.S. Cl. ....................................................... 73/841
(58) Field of Classification Search ........... 73/862.046, 73/841
See application file for complete search history.

(56) References Cited

U.S. PATENT DOCUMENTS

| | | | | |
|---|---|---|---|---|
| 5,571,973 | A * | 11/1996 | Taylot | 73/862.046 |
| 5,606,136 | A * | 2/1997 | Kropp | 73/862.046 |
| 6,155,120 | A * | 12/2000 | Taylor | 73/862.046 |
| 6,216,545 | B1 * | 4/2001 | Taylor | 73/862.046 |
| 6,543,299 | B2 * | 4/2003 | Taylor | 73/862.046 |

* cited by examiner

*Primary Examiner*—Max Noori
(74) *Attorney, Agent, or Firm*—William L. Chapin

(57) ABSTRACT

A normal force gradient/shear force sensor device and measurement method for measuring internal stresses in tissues of a person supported by a chair or bed includes a planar matrix array of peripheral normal force sensors radially spaced from central shear force sensors, comprising an electrically conductive disk located within a circular opening bordered by circumferentially spaced apart electrodes. The disk and electrodes are located between upper and lower cover sheets made of a stretchable material such as polyurethane; one cover sheet is adhered to the disk and the other sheet is adhered to a support sheet for the electrodes. Motion between the cover sheets in response to shear forces exerted on the array causes the disk to press more or less tightly against the electrodes varying electrical conductance between the disk and electrodes proportionally to the magnitude and direction of the shear force. Each normal force sensor includes an electrically conductive film pressed between row and column conductors. Measurements of conductance values of pairs of sensor, which vary proportionally to normal forces exerted on the sensor, are used to calculate a gradient vector of normal forces exerted by a body part on the sensor array, which is combined with the shear force vectors in an algorithm to calculate internal reaction shear forces, e.g., on flesh near a bony prominence.

20 Claims, 15 Drawing Sheets

① AREA OF MAXIMUM PRESSURE GRADIENT AND AREA OF MAXIMUM INTERNAL TISSUE STRAIN

VERTICAL SECTION $\bar{S}$ = TOTAL INTERNAL SHEAR $F_{SE}$ = EXTERNAL SHEAR FORCE VECTOR $\theta$ = ANGLE FROM $F_{MAX}$ (CENTER) AND THE MAXIMM FORCE GRADIENT $F_{GR} = F_{MAX}$

EQUATION $$\bar{S} = F_{SE} * \sin\theta \cdot \hat{i} + F_{SE} * \cos\theta \cdot \hat{j} + F_{GR} \cdot \hat{k}$$

Ⓐ RIBBON CABLE WIRED TO EACH CF ROW & COLMN

Ⓑ 2X TAPE SEALING PERIMETER

Ⓒ SHEAR & NORMAL ARRAY $F_{NMAX} - F_{NMIN} = F_{NMIN}$ -THE SMALLEST
OF $F_a ... F_i$ $F_{NMAX} - F_{NMIN}$ IS ADDITIVE TO $F_{SE}$ ONLY
WHEN IN THE SAME DIRECTION

NORMAL FORCE GRADIENT/SHEAR FORCE SENSORS AND METHOD OF MEASURING INTERNAL BIOLOGICAL TISSUE STRESS

BACKGROUND OF THE INVENTION

A. Field of the Invention

The present invention relates to force sensing transducers, sensor arrays and apparatus, and methods employing force sensors to measure forces exerted on biological tissues. More particularly, the invention relates to novel shear and normal force sensors and arrays thereof for measuring normal force gradients and surface tangential shear forces exerted on surfaces of human tissue, and a method for measuring shear forces exerted on internal tissues from normal force gradients and tangential shear forces measured by such sensors or arrays thereof.

B. Description of Background Art

In any instance where a human body is supported by a surface, there exists normal and shear forces exerted by the weight of the individual which are transmitted through the skeleton to the muscles, adipose tissue, skin, etc., to the support surface. The support surface exerts equal and opposite forces on the body, which can in some cases cause damage to tissues. The magnitude and duration of the forces that compress internal blood vessels and occlude nutrients from the tissue determine the length of time to tissue damage or morbidity. High pressure alone is generally not sufficient to deleteriously affect tissue. Deep-sea divers for example, are subjected to high, but evenly distributed normal forces and do not suffer from tissue damage. If, however, there is a sufficiently large external pressure gradient on a body part, resulting from, for example, a low-pressure area adjacent to a high-pressure area, internal body fluids can migrate to the area of lower pressure. Tangential or shear forces exerted externally on a body part can also collapse internal capillaries and blood vessels by distorting them along their longitudinal axis. It is therefore extremely important to know both the surface force gradient (pressure gradient) and the externally applied shear force exerted on tissue, because it is the combination of these factors that leads to tissue strain and subsequent tissue death. Thus, even relatively small external shear and normal forces, which may be independent of one another, can combine to produce damagingly large shear stresses on internal tissue. The areas of the human body which are most at risk of developing tissue damage such as a pressure sore are: heel, ischial tuberosities, greater trochanter, occiput and sacrum.

There are available a variety of pressure/force sensors, shear sensors and sensor arrays which are useable for measuring normal and shear forces exerted on human tissues. For example, the present inventor's U.S. Pat. No. 5,751,973, Nov. 5, 1996, Multi-Directional Piezoresistive Shear And Normal Force Sensors For Hospital Mattresses And Seat Cushions discloses thin, planar sensors for measuring reaction forces exerted by mattresses or chair pads on the body of a recumbent or seated patient. One embodiment of the invention disclosed in the specification of the '973 patent includes a sensor comprised of a two-dimensional array of isolated sensor element pads, each consisting of a thin, flat layer formed of a non-conductive elastomeric polymer matrix filled with electrically conductive particles. A matrix of upper and lower conductive elements in electrical contact with upper and lower sides of each sensor pad enables separate measurements to be made of the electrical resistance of each pad. Pressure exerted on each pad, e.g., in response to a normal force exerted on the sensor matrix by a person's body, reduces the thickness of the sensor pad, and therefore its electrical resistance by a bulk or volume piezoresistive effect.

The present inventor also disclosed a novel method and apparatus for measuring pressures exerted on human feet or horses' hooves in U.S. Pat. No. 6,216,545, Apr. 17, 2001, Piezoresistive Foot Pressure Measurement. The novel apparatus disclosed in the "545 patent includes a rectangular array of piezoresistive force sensor elements encapsulated in a thin, flexible polymer package. Each sensor element includes a polymer fabric mesh impregnated with conductive particles suspended in an elastomeric matrix such as silicone rubber. The piezoresistive mesh layer is sandwiched between an array of row and column conductor strip laminations, preferably made of a nylon mesh impregnated with printed metallic paths. Each region of piezoresistive material sandwiched between a row conductor and column conductor comprises an individually addressable normal force or pressure sensor in a rectangular array of sensors, the resistance of which varies inversely in a pre-determined way as a function of pressure exerted on the sensors, and thus enabling the force or pressure distribution exerted by an object contacting the array to be mapped.

In U.S. Pat. No. 6,543,299, Apr. 8, 2003, Pressure Measurement Sensor With Piezoresistive Thread Lattice, the present inventor disclosed a transducer sensor array for measuring forces or pressures exerted on a surface, the array including a fabric-like, two-dimensional lattice of individual force or pressure sensor transducer elements comprising intersecting regions of pairs of elongated, flexible threads, each consisting of a central electrically conductive wire core covered by a layer of piezoresistive material which has an electrical resistivity that varies inversely with pressure exerted on the material.

The shear and normal force sensors and arrays described above are useful in producing maps of normal and shear forces exerted at discrete points on a surface, such as a human body part, by an object, such as the supporting surface of a chair. However, there remains the problem of providing an apparatus and method for measuring shear forces and stresses on portions of human tissue which are located some distance below the surface of skin. The present invention was conceived of to fulfill that need.

OBJECTS OF THE INVENTION

An object of the present invention is to provide a transducer type sensor for producing electrical signals which are proportional to shear forces and normal force gradients exerted on the surface of a human body part by the surface of an object such as that of a chair or other supporting surface, and a method for determining from the surface shear and normal force gradients shear forces exerted on tissue located below the surface of the body part.

Another object of the invention is to provide a normal force gradient/shear force sensor array for measuring distribution of shear forces and normal force gradients on an area of a human body part, and determining from those measurements shear forces exerted on tissue below the area.

Another object of the invention is to provide a normal force gradient/shear force sensor array and method for determining subsurface shear forces in internal biological tissue located beneath the surface of a human body part.

Various other objects and advantages of the present invention, and its most novel features, will become apparent to those skilled in the art by perusing the accompanying specification, drawings and claims.

It is to be understood that although the invention disclosed herein is fully capable of achieving the objects and providing the advantages described, the characteristics of the invention described herein are merely illustrative of the preferred embodiments. Accordingly, I do not intend that the scope of my exclusive rights and privileges in the invention be limited to details of the embodiments described. I do intend that equivalents, adaptations and modifications of the invention reasonably inferable from the description contained herein be included within the scope of the invention as defined by the appended claims.

SUMMARY OF THE INVENTION

Briefly stated, the present invention comprehends a novel sensor device, and an array of such sensor devices, for measuring, respectively, a shear force and normal force gradient at a discrete location or at a two-dimensional matrix of locations on the surface of a human body part, and a method of determining from those measurements internal subsurface shear forces exerted on biological tissue at a discrete location or matrix of locations.

According to the invention an individual normal force gradient/shear force sensor assembly has a layered or laminated structure that includes a thin, flexible sandwich of electrically conductive elements and insulating elements, which are encapsulated between thin, flexible upper and lower cover sheets made of an insulating polymer such as polyurethane. Each sensor assembly includes a centrally located shear force sensor which is bordered by adjacent peripheral or satellite normal force sensors that are used to measure normal force gradients. Preferably, each normal force gradient sensor assembly includes at least two adjacent normal force sensors on at least three, and optionally four sides of the central shear force sensor, so that normal force gradients may be determined in all spatial directions in a two-dimensional plane. Each normal force sensor is comprised of an upper conductor strip which comprises an upper electrode, a lower conductor strip which comprises a lower electrode, and an intermediate layer located between the upper and lower conductor strips, the intermediate layer having an electrical property which varies in a predetermined way with normal force exerted on the sensor. In a preferred embodiment, the intermediate layer of each normal force sensor is made of a material which is relatively poor electrical conductor, or "semiconductor." Pressing the semiconductor material between upper and lower normal force electrodes in response to normal forces exerted on the sensor causes more intimate contact between the electrodes, which preferably have a relatively good conductivity, and the semiconductor material. This construction causes the electrical conductivity of the normal force sensor to increase proportionally to normal pressure urging the intermediate semiconductor layer into more intimate contact with the sensor electrodes, an effect which may be described as "surface piezoresistivity." A preferred embodiment of normal force sensors according to the present invention uses an intermediate semiconductive layer made of a resilient polymer, such as a polyolefin, which is "doped" or "filled" with an electrically conductive substance such as finely divided carbon granules. An example of a semiconductive material suitable for use on a piezoresistive layer material found suitable for the present invention was a carbon filled polyolefin which had a surface resistance of about $10^5$ ohms per square. It should be noted that resilient semiconductor materials such as the carbon-filled polyolefin described above may also display volume piezoresistive effects resulting from compression of the material. In any event, poorly conductive or semiconductive materials with the properties described above are referred to hereinafter as "piezoresistive."

The central shear force sensor of each normal force gradient/shear force sensor assembly according to the present invention includes "bung" which is located concentrically within an opening formed between radially inwardly protruding edge ends of a plurality of flat, electrically conductive strips, which comprise the electrodes for the shear force sensor. The plate or bung is preferably made of a material which is a relatively poor electrical conductor, such as the semiconductive materials used in the normal force sensor as described above. Moreover, the bung material may have a piezoresistive property, as described above. In a preferred embodiment, the plate or bung has the shape of a circular disk, and is positioned coaxially within a circular opening bordered by spaced apart conductive strips which serve as electrodes for the shear force sensor. In a preferred embodiment, three shear force conductor strips are provided, but a different number, such as four may be used, as long as a sufficient number and arrangement of shear force conductor strips or electrodes are provided to be able to detect shear force-caused relative motion between the center bung and electrodes, in all spatial directions in a two-dimensional plane.

The central shear force sensor also includes electrically conductive elements held between upper and lower cover sheets made of a thin, stretchable, electrically non-conductive material such as polyurethane. In a preferred embodiment of a combined shear force/normal force gradient sensor array according to the present invention, shear force sensors are arranged in a rectangular or square matrix within a matrix of peripheral normal force sensors. In this embodiment, the peripheral normal force sensor elements are comprised of a sheet of piezoresistive material sandwiched between a plurality of lower parallel, transversely spaced apart flexible longitudinally disposed row electrodes fastened to the upper surface of a lower polyurethane cover sheet, and a plurality of upper, parallel, longitudinally spaced apart flexible horizontally disposed column electrodes. The latter are attached to the lower surface of an intermediate polyurethane sheet which serves as a bottom or base support sheet for individual shear force sensor assemblies.

Each shear force sensor assembly preferably includes a central normal force sensor which is located below or above a shear force sensor, with the center of the circular opening of the shear force sensor axially or vertically aligned with the center of the central normal force sensor below it. The central normal force sensor consists of a thin, transversely elongated flexible rectangular conductor attached to the upper surface of an intermediate polyurethane sheet and which is overlain by a small rectangular pad of piezoresistive material on which rests a thin, flexible, longitudinally disposed central normal force row conductor strip. Lower and upper surfaces of the central normal force sensor piezoresistive pad are contacted by the lower transversely disposed central normal force column conductor strip, and the upper row conductor strip, respectively. The piezoresistive pad for the central normal force sensor has adhered to the upper surface thereof the lower surface of a thin insulating sheet of an insulating material such as double-stick tape.

The thin insulating sheet has a square shape and has formed through its thickness dimension a central square, concentric perforation, giving the sheet the shape of a "square annular" ring. The upper surface of the square annular ring is adhered to the lower surface of the upper longitudinally disposed row electrode conductor strip for the central normal force sensor, and functions to transmit shear forces upwardly from the lower portions of the sensor array through the row conductor strip, which serves as the base for the shear sensor.

The row conductor strip which serves as the base for the shear sensor slidably supports a flat annular ring made of Teflon, the upper surface of which is adhered to the lower surface of a circular disk-shaped center bung of the shear sensor. The bung is electrically conductively connected to the upper surface of the row conductor support strip/shear sensor base by a small, thin, circular disk-shaped "dot" which is located coaxially within the Teflon ring, the dot being made of a conductive fabric such as Chomerics PIN CFT-36-101 which is adhered to the row conductor strip and bung by a conductive adhesive such as contact cement filled with a minimum of 50% graphite powder or, preferably, a conductive adhesive applied to the conductive fabric as supplied by the manufacturer.

The shear force sensor includes an addition to the piezoresistive bung a peripheral electrode assembly for providing electrical signals which are related to shear force-induced movement of the bung relative to the electrode assembly. In a preferred embodiment, the shear force electrode assembly is fabricated as a plurality of planar electrodes comprising thin copper foils which are adhered to the upper surface of a thin, flexible insulating substrate sheet made of a material such as KAPTON. Preferably, the electrodes are arranged so that shear motion of the bung in any direction in a plane parallel to the substrate sheet, e.g., in an X-Y plane, may be detected. Thus, four electrodes arranged in a cross configuration including two longitudinally spaced apart, plus and minus X electrodes, and two transversely spaced apart, plus and minus Y, electrodes could be used. In a preferred embodiment which minimizes the number of required shear force sensor electrodes, three electrodes spaced circumferentially apart at 120-degree intervals are used, the electrodes having inner facing arcuately curved concave edges which are each segments of a circular arc having a length of slightly less than 120 degrees. With this arrangement, a continuous copper foil sheet on the upper surface of a KAPTON substrate sheet has etched through the foil three narrow elongated columns to form three isolated, generally rectangular shaped electrodes include a front left electrode, a central rear electrode, and a front, right electrode. A circular electrode hole punched through both copper foil and substrate sheet forms with the three electrodes a first, front left 120-degree circular arc segment wall, a second, centrally located rear 120 degree circular arc segment wall, and a third, front right, 120-degree circular arc segment wall. The arc segment walls lie on a cylindrical wall surface of the circular hole, which has a diameter about 0.001 inches larger than the bung, which is located coaxially within the hole in the absence of shear forces.

The upper surface of the piezoresistive bung has adhered to the upper surface thereof a coaxially located upper central shear force transfer disk made of double-stick tape, the upper surface of which is adhered to the lower surface of an upper stretchable polyurethane cover sheet. The shear force sensor also includes an outer upper shear force transfer ring which is made of double-stick tape. The outer upper shear force transfer ring has an annular ring-shape, including a central circular hole of larger diameter than piezoresistive bung, which is located coaxially within the outer upper shear force transfer ring. The upper surface of the shear force transfer ring is adhered to the lower surface of the stretchable polyurethane cover sheet, and the lower surface of the ring is adhered to the upper surface of the shear sensor electrode assembly. With this arrangement, motion of parts of the cover sheet adhered to the shear force transfer ring relative to a part of the sheet adhered to the central shear force transfer disk causes corresponding relative motion of the electrode assembly relative to the bung, e.g., in a fore-and-aft, transverse direction and a left-and-right, longitudinal direction relative to a horizontal reference plane containing the sensor.

The shear force sensor according to the present invention includes lead out conductors made of conductive fabric strips which are disposed between each of the three shear force sensor electrodes to an edge of the array, e.g., a front, rear, left or right edge of the array sheet.

When one terminal of a resistance measurement circuit is electrically connected to the piezoresistive bung of the shear force sensor and the lower conductor row electrode, shear force induced movement of the bung relative to the three shear force sensor electrodes produces measurable changes of resistance which can be ascertained by connecting a second terminal of the resistance measurement circuit separately to each of the three lead out electrodes. In a preferred embodiment resistance measurements are made to piezoresistive shear force sensor bungs as well as to piezoresistive sheets or pads of normal force sensors by a computer controlled multiplexer which sequentially connects a pair of resistance measuring circuit terminals to a pair of row and column conductors which intersect at an individual shear sensor or normal force sensor which it is desired to sample the resistance of.

In a preferred alternate embodiment of a sensor array described above, a central normal force sensor is not provided in vertical alignment with each individual shear force sensor. In this embodiment, pairs of peripheral normal force sensors are used to measure radial normal force gradients relative to the center of the shear sensors. Also in this embodiment, the piezoresistive pad and annular insulating square described above are dispensed with, and the column conductive fabric strip that was utilized as the column conductor for the central normal force sensor is utilized as the lead-out conductor for one of the three shear sensor electrodes, e.g., the rear center electrode.

According to another aspect of the present invention, a method for determining the magnitude of shear forces exerted on internal biological tissue utilizes an apparatus comprising a normal force gradient/shear force sensor array of the type described above, and an electronic control system for sequentially sampling and storing shear force measurement values made at discrete locations of the array, along with measurement values of normal forces at a plurality of locations radially spaced apart from each shear force measurement location, to thereby enable evaluation of normal force gradients in different radial directions from the shear force sensors.

An algorithm according to the invention utilizes shear force and normal force gradient values measured by the apparatus to infer internal tissues shear forces exerted on the body of a patient seated or recumbent upon a sensor array positioned between the patient's body and an upper surface of a supporting object such as a chair or bed.

The novel construction of a sensor array according to the present invention enables the array to have a small size and stretchable conformability to irregular surfaces which enable the array to determine the focus of force loads transferred from a bony prominence of a patient, such as a patient's heel, to an external support surface such as a bed mattress or chair. Thus, sensor arrays according to the present invention utilize a thin, conformable substrate made of a material such as a stretchable polyurethane, and thin, conductive fabrics, such as Flextron. Each shear sensor in an array includes a conductive fabric electrode assembly which has a central hole and arrangement of circumferentially spaced apart electrodes arranged around the hole, which are contacted by a central piezoresistive center bung movable by shear forces exerted on the array to contact the electrodes more or less tightly, thus providing an indication of the magnitude and direction of applied shear forces. Upper and lower surfaces of the sensor array are made to move with respect to their mating surfaces by a novel construction which is effective in managing frictional forces exerted between various elements of the sensor array. Moreover, central shear forces and peripheral normal forces are transmitted through the sensor array in a manner enabling both shear forces and normal force gradients to be measured independently.

An advantageous feature of novel shear/normal force sensor arrays according to the present invention is their ability to transfer shear and normal forces through the arrays without significant attenuation or cross-coupling. This capability is provided by allowing normal force sensing layers of the sensor array to float with respect to one another, and by forcing any tangential shear forces to be carried through the central bung.

Another advantageous feature of shear/normal force sensor arrays according to the present invention is a capability offered by the novel design of the array to be both very thin and readily conformable to irregularly shaped objects. While some prior art normal force sensors are relatively thin, shear force sensors have heretofore required relatively thick cross-sections. According to the present invention, a thin, copper coated fabric or plastic lamination serves as the electrode assembly for a shear force sensor which includes a piezoresistive bung located in a hole through the lamination, thus allowing peripheral normal forces to be transmitted through peripheral regions of the plane of the lamination, with sufficient spatial density to enable the measurement of normal force/pressure gradients. With this novel construction, the present inventor has constructed sensors as thin as 0.007 inch, and as small as 0.25 inch on a side, but it is believed that even smaller sensors may be constructed in accordance with the novel design of the present invention.

DESCRIPTION OF THE PREFERRED EMBODIMENTS

FIGS. 1–15 illustrate various aspects of individual normal force gradient/shear force sensors and sensor arrays according to the present invention.

Figure 1:
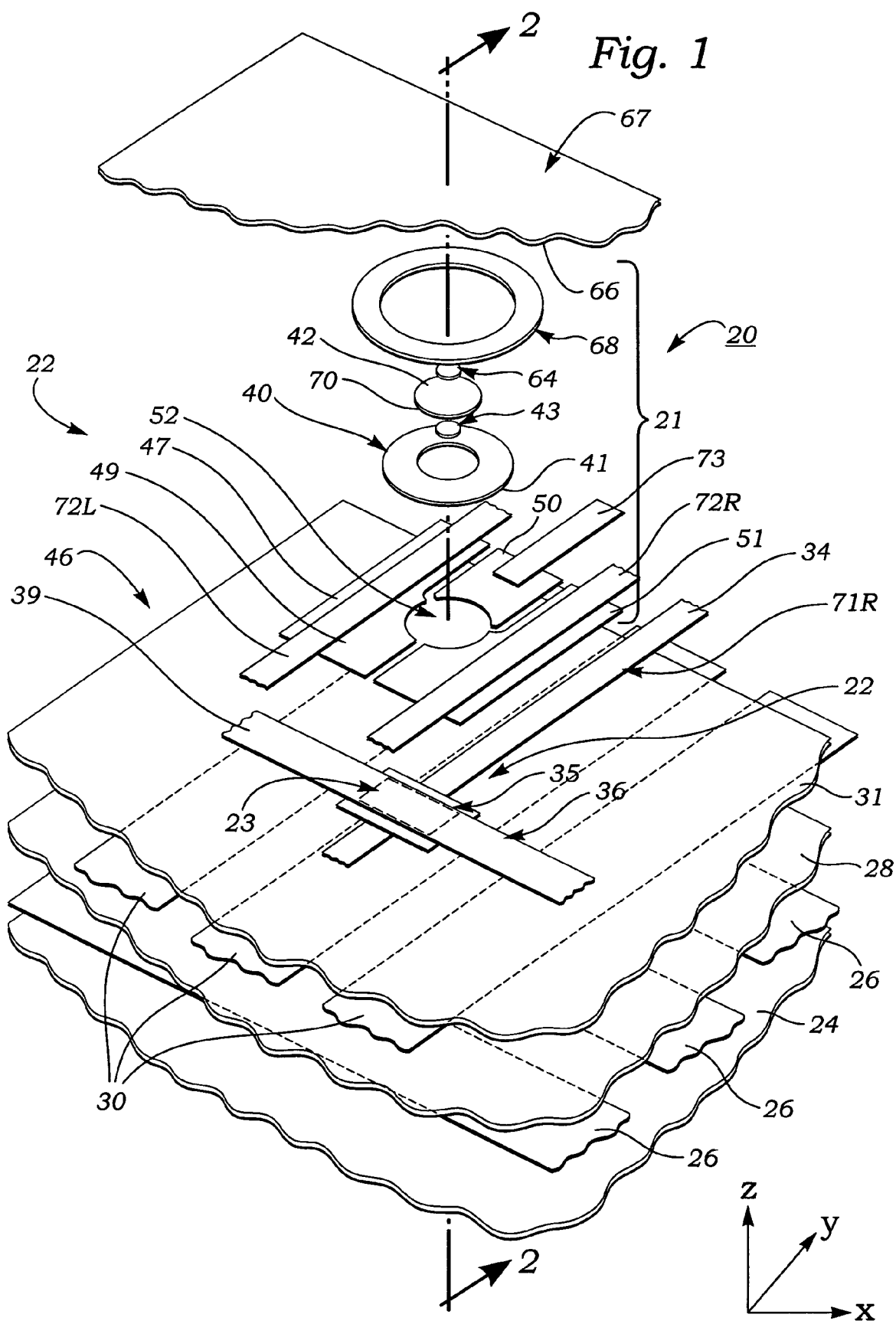
FIG. 1 is an exploded front perspective view of a normal force gradient/shear force sensor unit according to the present invention.
Figure 2:
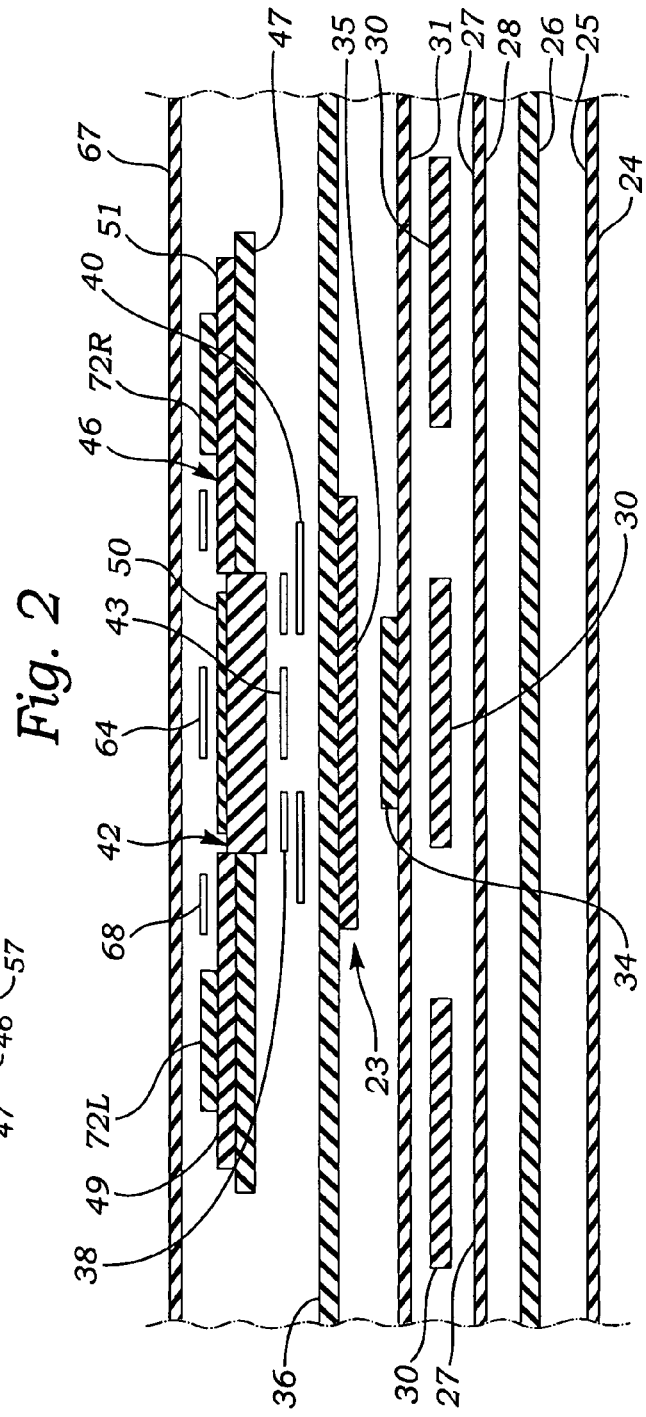
FIG. 2 is a front longitudinal cross sectional view of the sensor of FIG. 1, taken in the direction of line 2—2.

Referring first to FIGS. 1 and 2, those figures illustrate a normal force gradient/shear force sensor unit 20 consisting of a single shear force sensor 21, a plurality of associated peripheral normal force sensors 22, and a single central normal sensor 23 located below and vertically aligned with the shear sensor. As shown in FIG. 1, sensor unit 20 is comprised of a plurality of generally planar elements arrayed in parallel planes which, for convenience are defined as being parallel to an X-Y coordinate plane, and stacked in a vertical, Z direction. Thus, as shown in FIG. 1, sensor unit 20 includes a base, bottom or lower cover sheet 24 made of a thin flexible, stretchable sheet of an electrically non-conductive material. In an example embodiment of sensor unit 20, base sheet 24 was made of polyurethane having a thickness of about 0.002 inch, a modulus of elasticity of 1–2 $GP_A$, a tear strength of 475 $K_g/C_M$, and a specific gravity of 1.12; manufacturer's part no. Duaflex P/N PT9200, obtained from Deerfield Urethane (A Bayer Corporation), P.O. Box 196, South Deerfield, Mass. 01373.

As shown in FIG. 1, base sheet 24 has located on upper surface 25 thereof a plurality of longitudinally disposed, e.g., in a left-to-right or X-direction, parallel, longitudinally elongated, rectangularly-shaped, electrically conductive strips 26. As will be explained below, each row conductor strip 26 serves as a first, lower conductor for a pair of upper and lower of conductors used for each peripheral normal force sensor 22. Peripheral normal force sensor row electrodes 26 are each made of thin, flexible, electrically conductive material. In an example embodiment, row conductor strips 26 were made of a conductive fabric tape, part no. CFT-36-101, manufactured by Chomerics division of Parker Hannifin Corporation, 77 Dragon Court, Woburn, Mass. 01888-4014. In this example embodiment, each row conductor strip 26 for peripheral normal force sensors 22 had a width of about ½ inch, and was spaced about ¹⁄₁₆ inch apart in a fore-and-aft, or transverse direction from adjacent row conductor strips. The row conductor strips 26 were adhered to upper surface 25 of base sheet 24 by a conductive adhesive which coats one side of the conductive tape as supplied.

Referring still primarily to FIG. 1, it may be seen that each peripheral normal force sensor 22 of sensor unit 20 includes a piezoresistive element 27, which electrically conductively contacts the upper surface of a row conductor strip 26. In a preferred embodiment, the piezoresistive element 27 of each peripheral normal force sensor 22 comprises a separate rectangular, spaced apart area of a unitary piezoresistive sheet 28 which overlies and contacts the upper surfaces 29 of row conductor strips 26. In an example embodiment, piezoresistive sheet 28 consisted of an extruded sheet of carbon-filled polyolefin which had a thickness of about 0.002 inch, and was obtained from GE Polymer shapes, and identified by the trade name CONTRIM, had a specific gravity of 1.09, modulus of elasticity of 2 $GP_A$, surface and volume electrical resistivities of $10^5$ ohms/square and $10^5$ OHM-CM, respectively.

As shown in FIG. 1, each peripheral normal sensor 22 includes an upper, column electrode consisting of one of a plurality of transversely disposed, e.g., in a Y-direction, elongated, rectangularly-shaped, electrically conductive column conductor strips 30. Preferably, column conductor strips 30 have a size, shape, spacing and composition similar to that of row conductor strips 26. In a preferred embodiment, adhesive coated upper sides of column conductor strips 30 are adhered to the lower surface 32 of an intermediate polyurethane cover sheet 31 which is substantially similar in size and composition to base sheet 24.

Figure 1A:
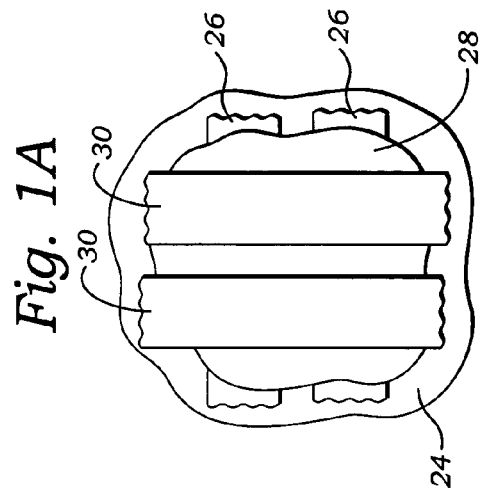
FIG. 1A is a fragmentary upper plan view of the sensor unit of FIG. 1 showing the arrangement of row and column conductor strips of peripheral normal force sensors of the sensor unit.

As shown in FIG. 1A, each area 27-RC of piezoresistive sheet 28 defined between the intersecting region of a peripheral normal force sensor column conductor strip 30-C overlying a row conductor strip 26-R comprises with vertically aligned areas of the conductor strips a discrete peripheral normal force sensor 22-RC, where R and C indicate integers. Thus, for example, the intersections of first and second adjacent row conductors 26-1, 26-2 with column conductor strips 30-1, 30-2 forms a square matrix of areas 27-11, 27-12, 22-21, 27-22 of piezoresistive sheet 28 which form four force sensors 22-11, 22-12, 22-21, 22-22, respectively. As will be described in greater detail below, connecting the two terminals of a resistance or conductance measurement circuit to a selected pair of row and column conductor strips 26-R, 30-C, enables the measurement of the resistance or conductance of any peripheral normal sensor 22RC in a two-dimensional matrix defined by the row and column conductor strips. FIG. 1B shows a typical variation of conductance versus pressure or normal force applied to a sensor 22.

Figure 10:
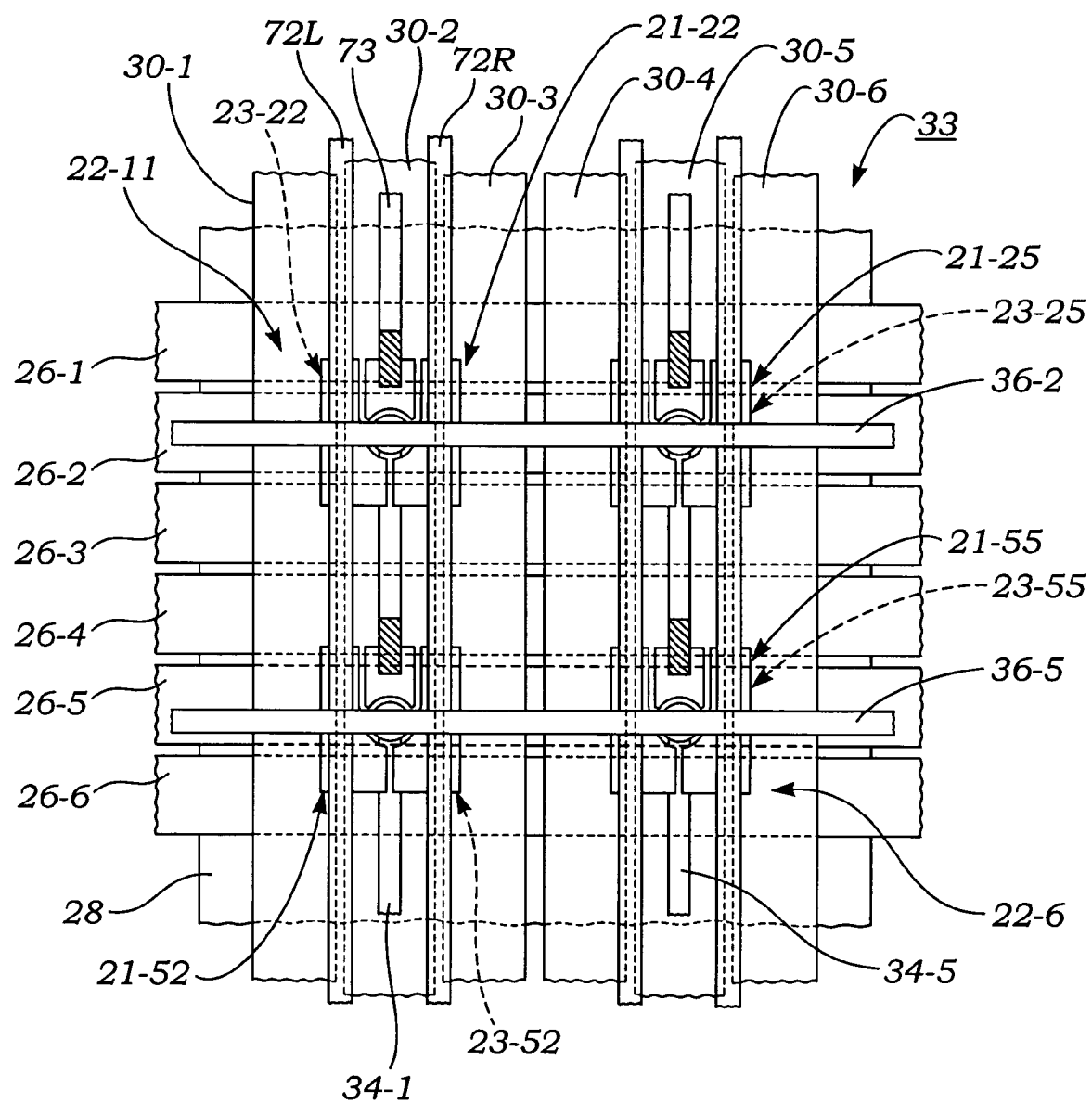
FIG. 10 is a diagrammatic fragmentary plan view of the sensor array of FIG. 9.

Referring to FIG. 10 in addition to FIGS. 1 and 2, it may be seen that peripheral normal sensors 22 are preferably arranged in an array 33 comprised of a plurality of sensors 22 located at intersections of row conductor strips 26 and column conductor strips 30. As shown in FIG. 10, array 33 includes a plurality of shear force sensors 21 which are located at transversely and longitudinally spaced apart matrix points of row and column conductor strips 26, 30, respectively, forming peripheral normal force sensors 22. For example, as shown in FIG. 10, shear force sensors 21 are located at the intersection of every fourth row electrode 26 and every fourth column electrode 30. With this arrangement, an array 33 including an m×m square matrix of peripheral normal force sensors 21 contains an m/2×m/2 matrix of shear force sensors 21, i.e., an n×n matrix, where n=m/2. Thus, a fragmentary portion of an array 33 shown in FIG. 10 containing 4×4=16 peripheral normal force sensors 22 contains a matrix of 2×2=4 shear force sensors 21.

In the embodiment of sensor array 33 shown in FIGS. 1, 2 and 10, which includes a central normal force sensor 23 vertically aligned with each shear force sensor 21, each central normal force sensor includes a lower, column conductor strip 34 made of conductive fabric tape. Conductor strip 34 is adhered to the upper surface 31U of intermediate polyurethane cover sheet 31 for peripheral normal force sensors 22, the intermediate polyurethane cover sheet serving as a base for central normal force sensors 23 and overlying shear force sensors 21. As shown in FIGS. 1 and 2, each central normal force sensor 23 includes a rectangularly-shaped sheet or pad 35 of piezoresistive material, which preferably has a composition substantially similar or identical to that of piezoresistive sheet 28 of peripheral normal force sensors 22.

Each central normal force sensor 23 also includes an upper, row conductor strip 36 which is also adhered to upper surface 31U of intermediate polyurethane base sheet 31. Column and row conductor strips 34, 36 comprise at vertically aligned intersections thereof column and row electrodes for central normal force sensors 23. Preferably, column and row central normal force sensor conductor strips 34, 36 are made of the same conductive fabric cloth as row and column conductor strips 26 and 30 for peripheral normal force sensors 21, and described above. However, central normal force sensor column and row conductor strips 34, 36 preferably are narrower than peripheral normal force conductor strips 26, 36, e.g., ⅛ inch wide and ¼ inch wide, respectively, instead of the ½ inch width of the peripheral normal force conductor strips. As shown in FIG. 10 and as will be described in detail below, the reduced width of conductor strips 34, 36 for central normal force sensors 23 allows space for additional conductor strips required for shear force sensors 21.

Referring still to FIGS. 1 and 2, it may be seen that each intersection of a column conductor strip 34 and row conductor strip 36, in combination with a piezoresistive pad 35 sandwiched between the conductor strips, forms a separate central normal force sensor 23, and has located between the piezoresistive pad and the overlying row conductor strip a concentrically located, annular square 38. Square 38 functions as a lower shear force transfer element, and augments transfer of shear forces from the upper surface of piezoresistive sheet 28 through intermediate polyurethane sheet 31 and through central normal sensor 23 to the upper surface 39 of row conductor strip 36.

Referring again to FIGS. 1 and 2, it may be seen that a separate shear force sensor 21 is stacked on top each central normal force sensor 23. Each shear force sensor 21 includes a first, lower conductor strip which in the embodiment shown in FIGS. 1–3, comprises a central normal force row conductor strip 36. Row conductor ship 36 for a central normal force sensor 23 and shear force sensor 21 slidably supports a flat annular ring 40 made of a slippery material such as TEFLON. The upper surface of Teflon ring 40 is adhered to the lower surface of a circular disk-shaped pad or bung 42 which is the central movable element of a shear force sensor 21. Bung 42 is made of a piezoresistive material similar or identical in composition to piezoresistive sheet 27 and pad 35, and has a lower surface which is adhered to the upper surface of Teflon ring 40 by an annular ring-shaped piece of double-stick adhesive tape 41. In an example embodiment of a shear force sensor 21, center bung 42 had a diameter of about ¼ inch and a thickness of about 0.006 inch. Center bung 42 is electrically conductively connected to row conductor strip 36, as for example, by a conductive fabric dot 43 electrically conductively adhered to both lower surface 44 of the bung, and upper surface 45 of the row conductor strip.

Each shear force sensor 21 includes, in addition to piezoresistive center bung 42 a peripheral electrode assembly 46. In a preferred embodiment shear force electrode assembly 46 is fabricated as a plurality of planar electrodes comprising thin copper foil which are adhered to the upper surface 48 of a thin, flexible electrically non-conducting substrate sheet 47 made 26 of a material such as KAPTON. Thus, as shown in FIGS. 1, 1C, 2 and 10, shear force electrode assembly 46 includes a generally rectangularly-shaped substrate sheet 47 of Kapton having a length of about 1.2 inch, a width of about ½ inch, and a thickness of about 0.002 inch. Adhered to the upper surface 48 of substrate sheet 47 are a plurality of electrodes made of copper foil having a thickness of about 0.001 inch.

Figure 1C:
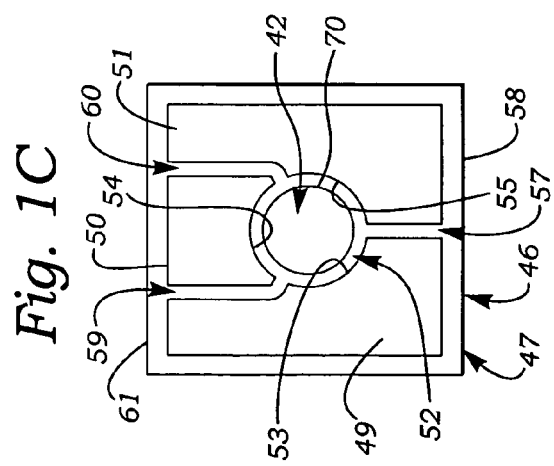
FIG. 1C is an upper plan view on an enlarged scale of an electrode assembly for a shear sensor of the sensor unit of FIG. 1.
Figure 1B:
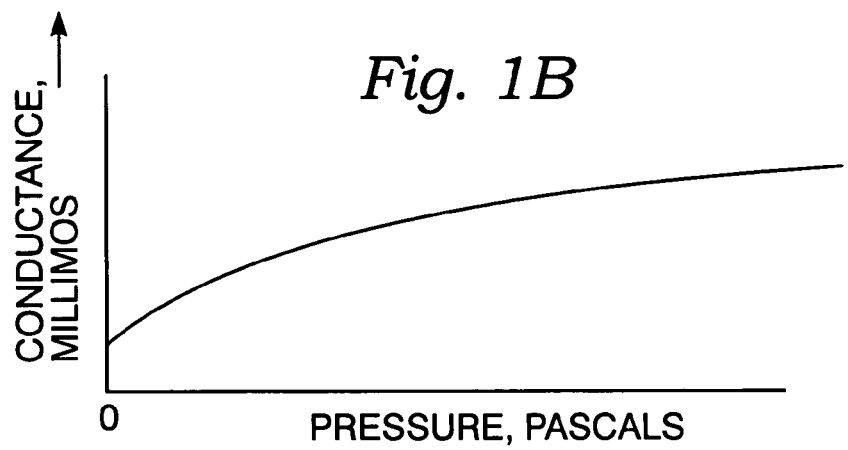
FIG. 1B is a graph showing the variation of electrical conductance versus applied normal force/pressure on a peripheral normal force sensor of the sensor unit of FIG. 1.

As shown in FIGS. 1, 1C and 10, each shear force sensor 21 has 3 electrodes, including a left electrode 49, a rear center electrode 50, and a front right electrode 51. The three electrodes have inner facing surfaces which border a hole 52 through the thickness dimension of substrate sheet 47. Thus, as shown in FIGS. 1, 1C and 10, front left electrode 49 has at a rear right edge thereof a concave surface 53 which has the shape of a circular arc segment having a length of slightly less than 120 degrees. Similarly, rear center electrode 50 has a circular arc segment-shaped front concave contact surface 54 which borders the periphery of hole 52, and also has an arc segment length of slightly less than 120 degrees. Also, front right electrode 51 has at a rear left-hand corner thereof a circular arc segment-shaped surface 55 which borders the periphery of hole 52, and also has an arc length segment of slightly less than 120 degrees. The centers of contacting edges of 53, 54, 55 of electrodes 49, 50, 51 are spaced circumferentially apart at 120-degree intervals, the contacting edges forming three electrically isolated portions of a cylindrical wall surface 56 of hole 52.

As shown in FIGS. 1, 1C and 10, front left and front right electrodes 49 and 51 of shear force sensor 21 have generally rectangularly-shaped vertically disposed front portions which are spaced apart longitudinally from one another by a transversely disposed, rectangularly shaped gap 57 which extends rearwardly from the front edge 58 of substrate sheet 47 to hole 52. Also, rear center electrode 50 of shear force sensor 21 is spaced apart from upper portions of left and right electrodes 49 and 51 by left and right transversely disposed, constant width gaps 59 and 60 which extend forward from rear edge 61 of substrate sheet 47 for most of the length of the gaps, and then turn radially inwardly to terminate at hole 52. The intersections of gaps 57, 59 and 60 with hole 52 are spaced apart at 120-degree circumferential intervals, and electrically isolate the three electrodes 49, 50, and 51 from one another.

In a preferred embodiment, shear force sensor electrode assembly 46 is fabricated as a printed or etched circuit in which gaps 57, 59, 60 are made by etching through a sheet of copper foil 62 adhered to substrate sheet 47, whereupon hole 52 is formed through both the copper foil sheet and substrate. Optionally, edges 53, 54 and 55 of electrodes 49, 50, 51, which are contactable by the circumferential surface of bung 42 in response to radial movement of the bung relative to the electrodes in response to shear forces applied to shear sensor 21, may be processed to provide an electrically uniform surface, as for example, by plating the cylindrical wall surface 56 of hole 2 after it has been bored.

Referring now to FIGS. 1 and 2, it may be seen that the upper surface 63 of shear force sensor bung 42 has adhered thereto a coaxially located upper central shear force transfer disk 64. Upper central shear force transfer disk 64 is preferably made of double-stick tape, the upper surface of which is adhered to the lower surface 66 of a sensor unit upper cover sheet 67 which is made of a stretchable polyurethane similar or identical in composition and size to lower cover sheet 24 and intermediate cover sheet 31.

Referring still to FIGS. 1 and 2, it may be seen that each shear force sensor 21 also includes an outer upper shear force transfer ring 68 which is also preferably made of double-stick tape. Outer upper shear force transfer ring 68 has an annular ring-shape which includes a central coaxially located circular hole 69 of larger diameter than piezoresistive bung 42. The lower surface of outer upper shear force transfer ring 68 is adhered to the upper surface of shear force electrode assembly 46, in coaxial alignment with hole 52 through the electrode assembly. The upper surface of outer upper shear force transfer ring 68 is adhered to lower surface 66 of stretchable upper cover sheet 67. With this arrangement, motion of parts of cover sheet 66 adhered to shear force transfer ring 68 relative to a part of the cover sheet adhered to upper central shear force transfer disk 64 causes corresponding motion of center bung 42 of the shear force sensor relative to contacting edges 53, 54, 55 of electrodes 49, 50, 51, respectively. The latter relative motion in turn causes the circumferential edge 70 of bung 42 to press more or less tightly against edges 53, 54, 55 of the electrodes, thereby varying the electrical resistance or conductance between the bung and the electrodes in a pre-determined way, owing to a piezoresistive property of the center bung.

FIGS. 1, 2 and 10 illustrate the manner of making lead-out connections to center bung 42 and electrodes 49, 50, and 51 of each shear force sensor 21. As shown in those figures, lead-out conductors for left and right electrodes 49 and 51 of each shear force sensor 21 are comprised of conductive fabric strips 72L, 72R which are made of a conductive fabric cloth adhered by an electrically conductive adhesive to the upper surfaces of electrodes 49 and 51. Similarly, a central vertically disposed conductive fabric strip 73 serves as a lead-out connector to rear central shear force sensor electrode 50.

Figure 7B:
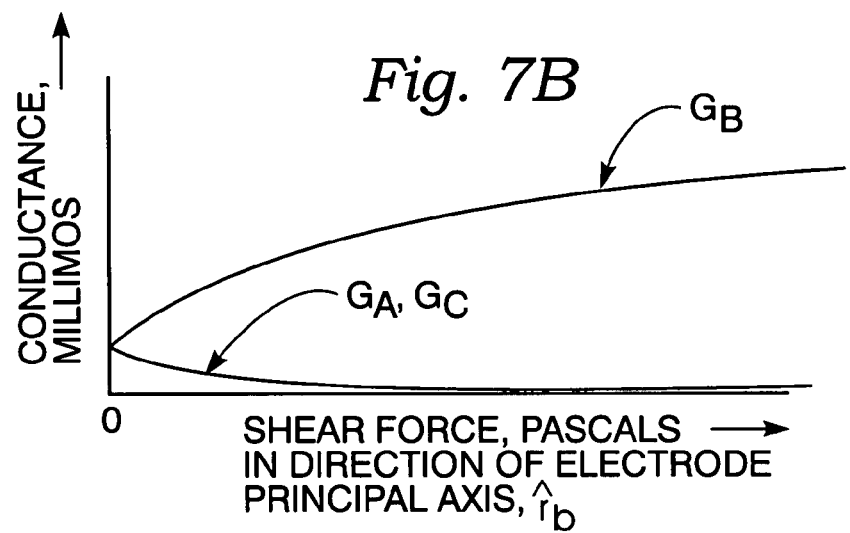
FIG. 7B is a graph showing the variation of electrical conductance between each of the three electrodes of a shear force sensor and the center bung of the sensor, versus shear motion parallel to one of the three 120-degree spaced apart sensitive axes of the sensor.
Figure 7C:
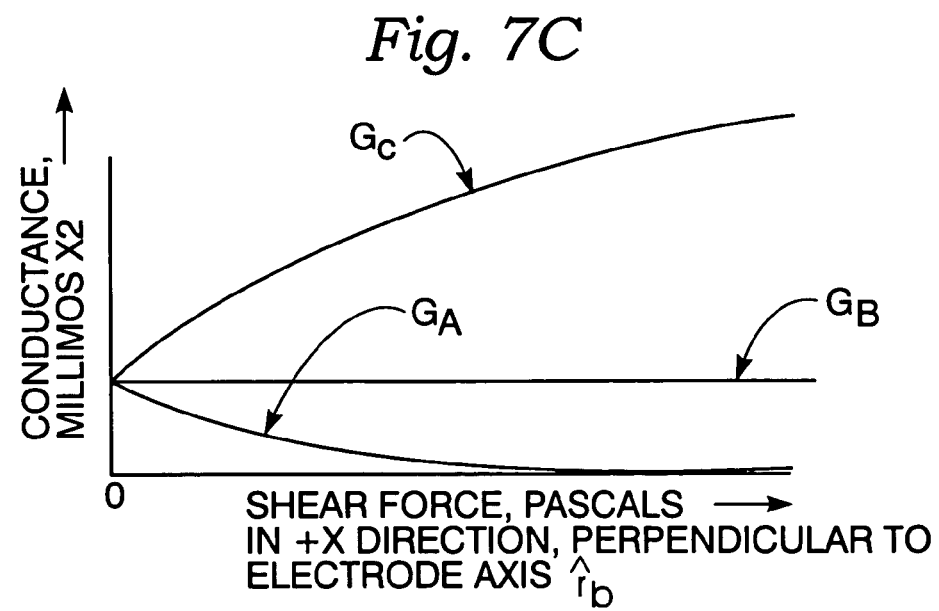
FIG. 7C is a graph similar to that of FIG. 7B, but for shear motion perpendicular to one of the sensitive axes of the sensor.
Figure 7A:
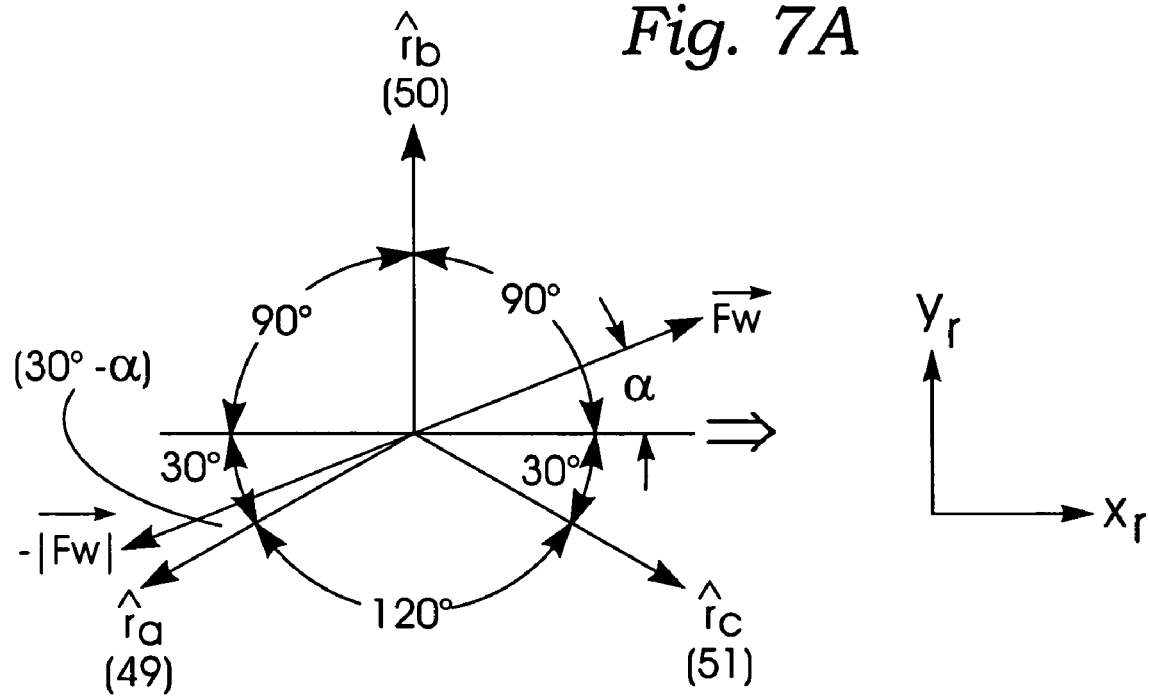
FIG. 7A is a diagrammatic view showing relations between shear force vectors exerted on the shear sensor of FIG. 1, and vector directions of three electrodes of the shear sensor.

FIG. 7A is a diagram showing the relative orientation of principal axes of sensitivity of electrodes 49, 50, and 51 of shear force sensor 21 and shear forces exerted thereon. FIGS. 7B and 7C are graphs which show the variation of electrical conductance between center bung 42 and each of the three electrodes 49, 50, 51 of shear force sensor 21, as a function of shear force couples being measured relative to lower surface 75 of lower stretchable cover sheet 24. FIG. 7B shows the variation of shear force sensor electrode conductance for shear force couples lying in a vertical plane which is perpendicular to the planes of the upper and lower sensor unit cover sheets, and which contains a line corresponding to the principal axis of sensitivity of a particular shear force sensor electrode. For example, referring to FIG. 1, a shear force couple lying in an Y-Z plane positioned midway within the vertically disposed gap 57 which separates front left electrode 49 and front right electrode 51 lies in a direction parallel to and in coincidence with the principal direction axis of sensitivity of rear central electrode 50.

FIG. 7C is a graph similar to that of FIG. 7B but shows variation of conductance between center bung 42 and shear force sensor electrodes 49, 50, and 51 for shear force couples lying in a plane perpendicular to a principal axis of sensitivity of a particular electrode. For example, shear force couples lying in a vertical X-Z plane through sensor unit 20 which bisects shear sensor electrode hole 52 are perpendicular to principal axis of sensitivity of rear central shear force sensor electrode 50.

Figure 4:
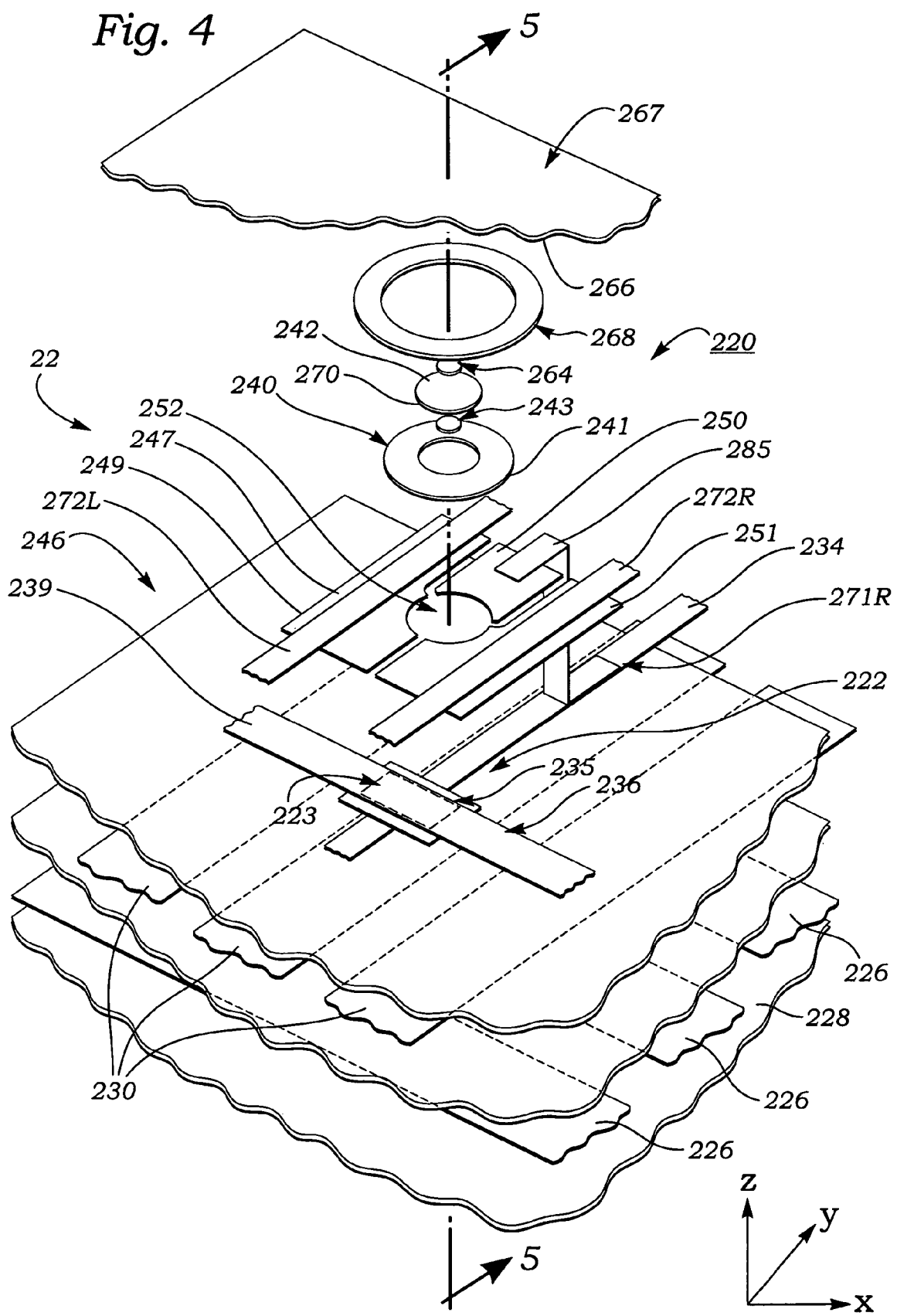
FIG. 4 is an exploded perspective view of an alternate embodiment of a normal force gradient/shear force sensor, which does not have a central normal force sensor.
Figure 5:
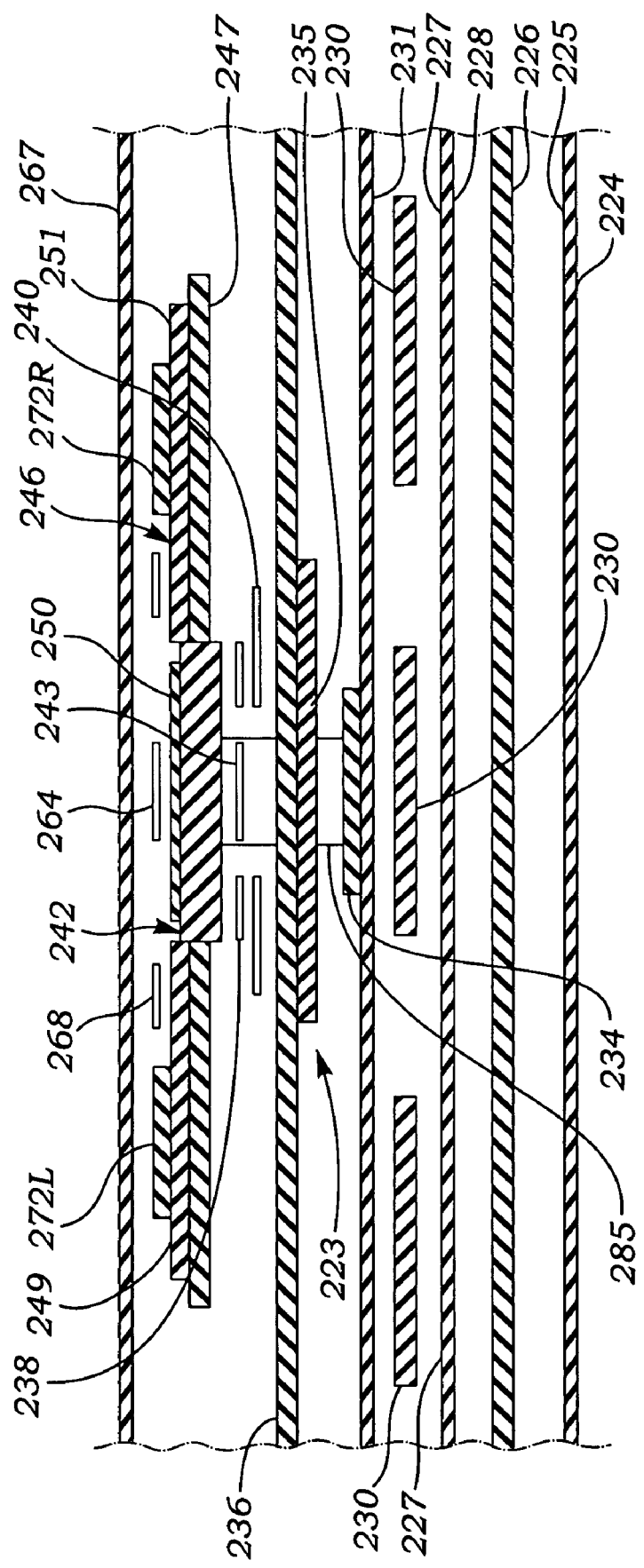
FIG. 5 is a front longitudinal cross-sectional view of the sensor of FIG. 4, taken in the direction of line 5—5.
Figure 6:
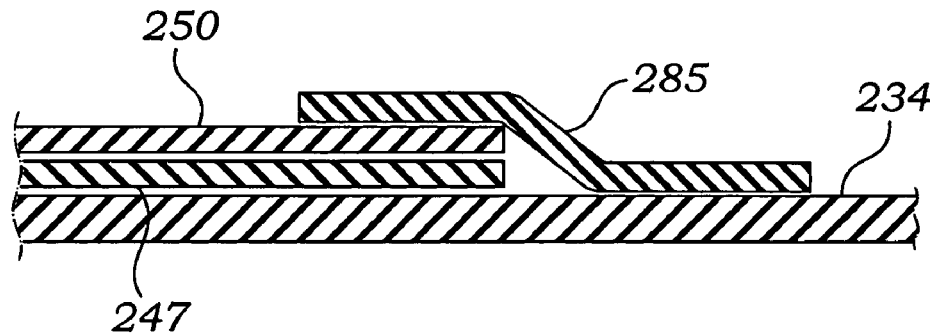
FIG. 6 is a side longitudinal sectional view of the sensor of FIG. 4, taken in the direction of line 6—6.

FIGS. 4–6 illustrate an alternate, simplified embodiment 220 of a normal force gradient/shear force sensor unit according to the present invention. Alternate embodiment 220 is substantially similar in construction and function to the basic embodiment 20 described above. However, alternate sensor unit 220 dispenses with central normal force sensors 23. Instead, simplified sensor unit 220 utilizes pairs of peripheral normal force sensors radially disposed in four directions from a shear force sensor 221 to determine normal force gradients at radially spaced apart locations from the shear force sensor. Thus, as shown in FIGS. 4–6, piezoresistive pads 35 of central normal force sensors 23 are replaced by insulating square sheets 235. This enables lower conductor strips 34 which were used as column conductors for central normal force sensors 23 in sensor unit 20, to be replaced in sensor unit 220 by similar column conductor strips 234 for use as lead-out connections to shear force electrodes. Thus, as shown in FIG. 6, lead-out conductor strip 234 is connected to, e.g., the rear central electrode 250 of each shear force sensor 221 by a strip of conductive fabric cloth 285.

Figure 11:
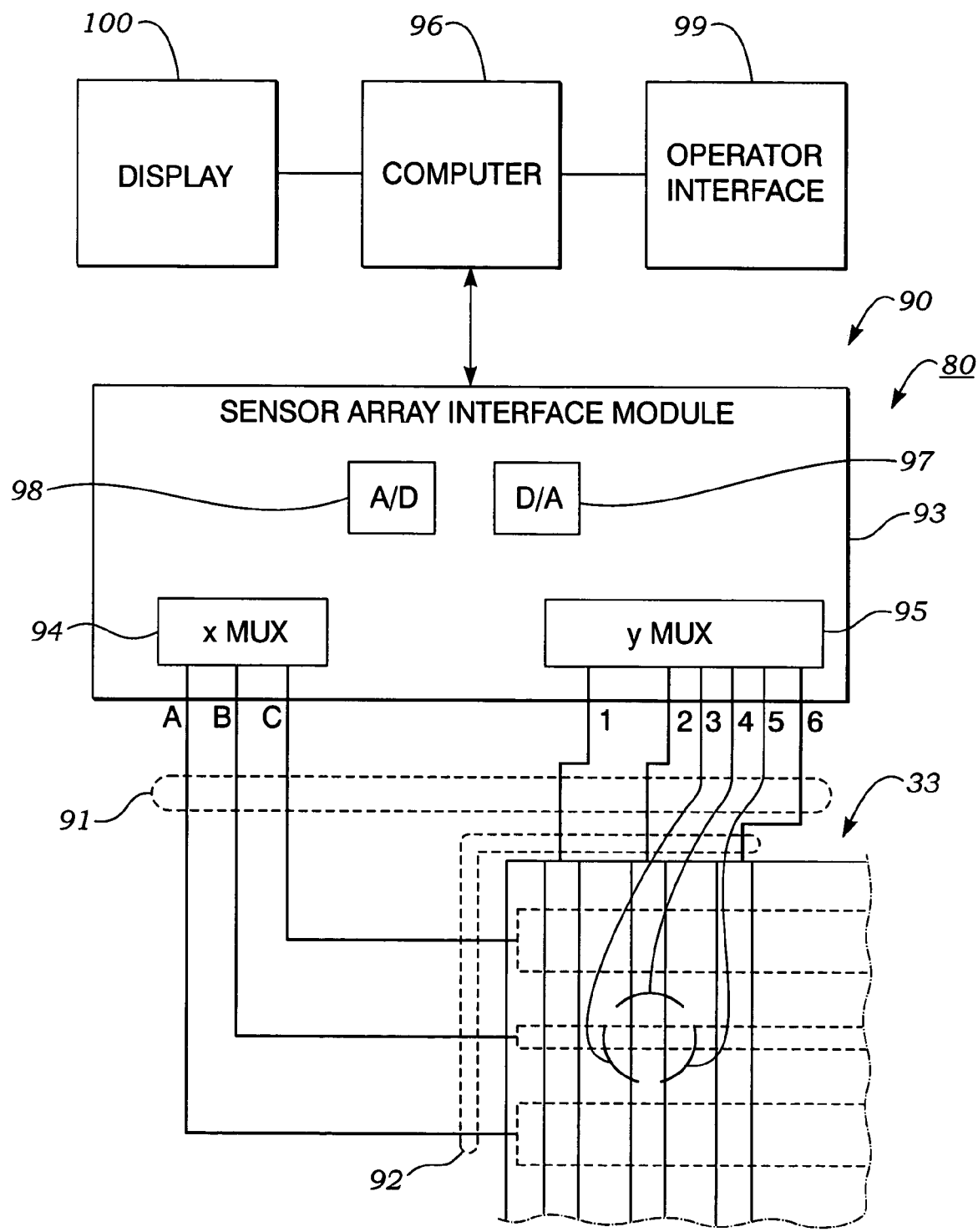
FIG. 11 is a schematic diagram of a normal force gradient/shear force sensor array measurement system according to the present invention.

FIG. 11 is a partially diagrammatic view showing a normal force gradient/shear force sensor array measurement system 80 according to the present invention. As shown in FIG. 11, measurement system 80 includes a normal force gradient/shear force sensor array 33 comprised of shear force sensor elements 21 and normal force sensor elements 22,23, of the type described above, and an associated electronic control, signal processing, and display apparatus 90, which is referred to hereafter as a sensor interface unit or apparatus.

As shown in FIG. 11, sensor interface apparatus 90 includes an interface cable 91 connected at one end thereof by a connector 92 to a sensor array 33. The other end of interface cable 91 is connected to a sensor array interface module 93 which provides means for applying electrical sampling signals between a selected column conductor strip 30 and row conductor strip 26 to thereby enable measurement of electrical conductance of a piezoresistive area located at the intersection of the column and row electrode strips, and thereby determine normal force or pressure exerted on a selected peripheral or central normal force sensor. Conductance is measured by applying a voltage of a known magnitude across a piezoresistive sensor, 22, 23, and measuring resulting current through the element, or by conducting a current of a known magnitude through the element, and measuring the resulting voltage drop across the element. An exactly similar measurement technique is used to measure the electrical conductances between the center bung 42 of a selected shear force sensor 21 and each of the peripheral electrodes, e.g., 49, 50, 51 of the shear force sensor to thereby determine the magnitude and directions of tangential shear forces exerted on the shear sensor. Although D.C. sampling voltages or currents can be used to measure the conductance of shear force sensors 21, peripheral normal force sensors 22 and central normal force sensors 23, alternating voltages or currents are preferably used to avoid potential polarizing effects on the sensor elements.

Interface module 93 preferably includes a first, row (x) multiplexer 94 and a e.g., second, column (Y) multiplexer 95. Multiplexers 94, 95 are caused to sequentially output a sequence of m×n addressing signals for the m rows and n columns of normal force sensors 22, 23, and a sequence of p×3q signals for addressing the three electrodes of p×q shear force sensors 21. For modified shear force sensors, which contain R electrodes rather than 3, such as the four-electrode shear sensors depicted in FIGS. 12–14 and described below, a sequence of m×(Rq) addressing signals would be output from interface module 93 to a sensor array, e.g., m×4q. Multiplexers 94, 95 are controlled by an internal clock and control logic (not shown) within sensor array interface module 93, or preferably, as shown in FIG. 11, by a computer 96, which will be understood by those skilled in the art, could be a general purpose computer, special purpose computer, microprocessor programmable logic control unit, or the like.

Referring still to FIG. 11, it may be seen that interface module 93 preferably includes a digital-to-analog converter (DAC) 97 to generate, under computer control, analog voltages or currents for application to individual sensors 21, 22, or 23 via multiplexer row and column lines m, n, and q. Also, sensor array interface module 93 preferably includes an analog-to-digital converter (ADC) 98 to measure currents through or voltages across a piezoresistive sensor element addressed by multiplexers 94, 95 and to which a voltage or current is applied. Measured values of currents through or voltages across individual piezoresistive sensor elements are output to computer 96. Computer 96 utilizes ratios of voltage drops across and currents through individual piezoresistive elements to thereby determine resistance or conductance of the element. Resistance or conductance values are then multiplied by predetermined scale factors $K_n$ or $K_s$ to calculate the normal force or pressure, or shear force, respectively, exerted on a particular sensor. In response to operational sequences selected by an operator interface device 99 such as a keyboard, mouse, or the like, computer 96 is directed to use a matrix of values of pressure and shear force measurements made at various matrix points of sensor array 33 for further signal processing. For example, a two-dimensional map of pressure and shear forces exerted on array 33 by a seated or recumbent patient may be displayed on a monitor 100, and/or stored in memory means for future viewing or processing. Preferably, and in accordance with another aspect of the present invention, values of shear and normal forces measured by the novel sensor arrays according to the present invention are utilized in a novel method to ascertain shear forces exerted on internal biological tissues of a patient, using an algorithm which is described in detail below.

Scale factors $K_n$ and $K_s$ may be calculated by any suitable method. One method of calculating $K_n$ consists of first employing measurement system 80 to measure the unloaded conductance of each electrode of each shear force sensor 21 and each normal force sensors 22 or 23 of an array 33 placed on a flat, horizontal support surface such as a table top. Then, a test object consisting of an air or oil-filled bladder is placed on top of the array, and conductance of each of the sensors measured as a function of at least two different weights of known magnitude placed on the test object, thus yielding values of $K_n$ for each normal force sensor 22 or 23, as well as any unwanted cross-coupling effects on the conductances of shear force sensors 21.

Values of $K_s$ for shear force sensors 21 are determined by utilizing a pair of parallel, flat rectangular plates placed underneath and on top of a sensor array, and exerting shear force couples of at least two different known magnitudes in at least two perpendicular directions parallel to the array, thus determining the overall or global sensitivity of the shear force sensors. A spherical indenter of a predetermined radius is then pressed against various places on the upper surface of the array with a sequence of at least two different transverse force magnitudes, to complete determination of shear force scale factors $K_s$.

Figure 12:
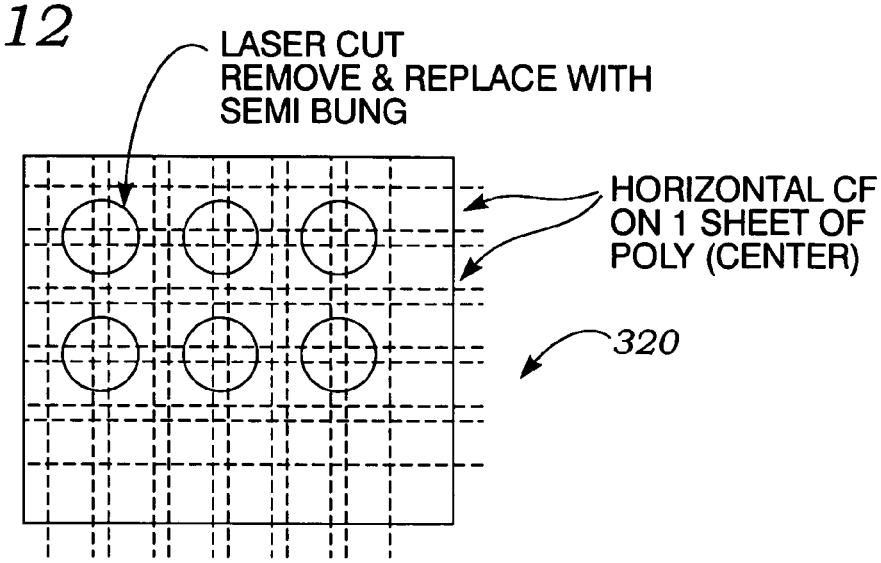
FIG. 12 is an upper plan view of a modified array of a shear force sensor according to the present invention, which uses four quadrant electrodes.
Figure 13:
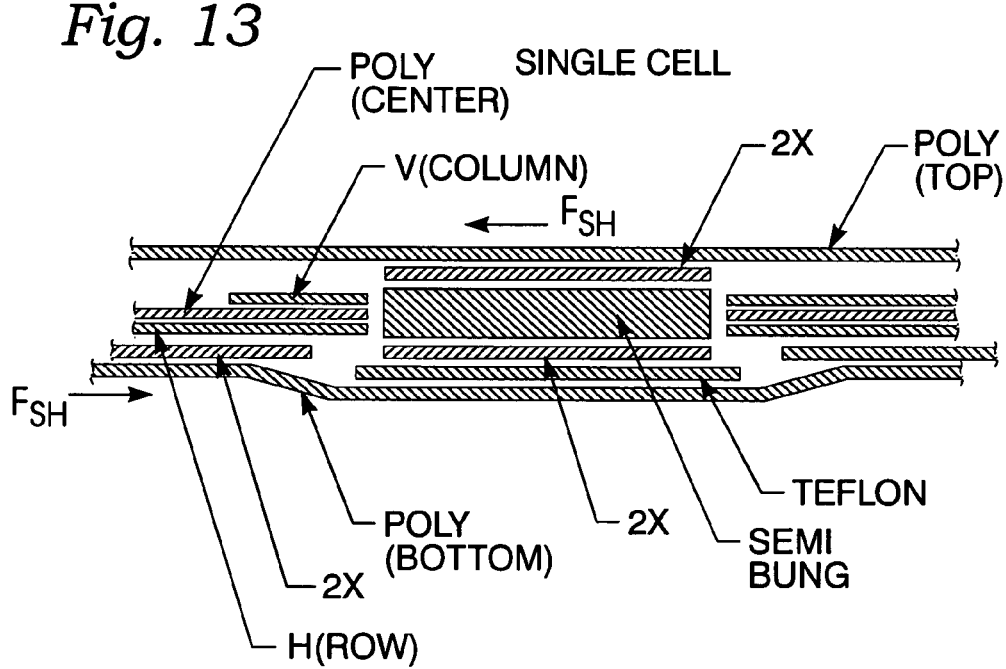
FIG. 13 is a vertical sectional view of the array of FIG. 12.

FIGS. 12 and 13 illustrate another embodiment 320 of a shear force sensor array according to the present invention, comprising a matrix of shear sensor force sensor 321 substantially similar in construction and function to shear force sensors 21 described above. Array 320 is useable by itself, but also with a normal force sensor array of the type shown in FIGS. 1 and 4 and described above.

As shown in FIGS. 12 and 13, modified shear force sensor array 320 includes a lower polyurethane base or cover sheet 324, an intermediate polyurethane sheet 331, and an upper polyurethane cover sheet 367 which are analogous in structure and function to elements 24, 31 and 67, respectively, of the basic embodiment of sensor unit array 33 shown in FIGS. 1, 2 and 10 and described above. Intermediate polyurethane sheet 331 has adhered to lower surface 332 thereof a plurality of longitudinally disposed, e.g., in a left-to-right or X-direction, parallel, longitudinally elongated, rectangularly-shaped row conductor strips 326 made of a conductive fabric. In an example embodiment of shear force sensor array 320, row conductor 11 strips 326 had a transverse width of ¼ inch, and were spaced apart at ¹⁄₃₂-inch transverse intervals.

As is also shown in FIGS. 12 and 13, intermediate polyurethane sheet 331 of shear sensor array 320 also has a plurality of longitudinally spaced apart column conductor strips 330 which are transversely disposed, e.g., in a Y-direction, adhered to upper surface 337 of sheet 331. Column conductor strips 330 have a transversely elongated rectangular shape, and are made of a conductive fabric of the same type used for row conductor strips 326. In an example embodiment of shear sensor array 320, column conductor strips 330 had a longitudinal width of ¼ inch, and were spaced apart at ¹⁄₃₂-inch longitudinal intervals.

As may be seen best by referring to FIG. 12, row and column conductor strips 326, 330 form a square matrix. Also, longitudinally disposed, rectangular gaps 326G between row conductor strips 326, and transversely disposed, rectangular gaps 330G between column conductor strips 330 form a square matrix of square vertically aligned intersection regions 380. As shown in FIGS. 12 and 13, a plurality of circular holes 381 are formed through upper column conductor strips 330, intermediate polyurethane sheet 331 and lower row conductor strips 326, each of the holes being concentric with a square gap intersection region 380. Holes 381 are made by any suitable means, such as by a die-cutting punch or laser. In an example embodiment of shear force sensor array 320, each hole 381 had a diameter of ¼ inch.

Referring now to FIG. 13 in addition to FIG. 12, it may be seen that each hole 381 of shear sensor array 320 has positioned coaxially therewithin a circular disk-shaped bung or pellet 342 made of a piezoresistive material. In an example embodiment of shear force sensor array 320, each piezoresistive bung had a diameter of 0.001 inch to 0.002 inch less than the diameter of hole 381, and had a thickness of about 0.008 inch. The bottom or lower surface 342B of bung 342 is adhered, e.g., by double stick tape to the upper surface 342U of a circular disk-shaped sheet 343 of TEFLON or other such slippery material, facilitating slidable contact of the bung and TEFLON disk on the upper surface 324U of polyurethane base cover sheet 324. The upper surface 342U of piezoresistive bung 342 is adhered, e.g., by double-stick tape, to the lower surface 367B of upper polyurethane cover sheet 367. Also, upper surface 324U of polyurethane base cover sheet 324 is adhered to lower surface 331B of intermediate polyurethane sheet 331 by a sheet of perforated rectangular-shaped sheets 385 of double-stick tape. With this construction, parallel translational motion of upper slidable polyurethane cover sheet 367 relative to lower stretchable polyurethane base cover sheet 324 causes corresponding translational movement of piezoresistive bung 342 relative to row and column conductor strips 326, 330, respectively. Motion of bung 342 relative to row and column conductor strips 326, 330, in turn causes piezoresistive conductive contact between the conductor strips, which conductance is proportional to the magnitude and direction of tangential shear forces exerted on sensor array 320, as will now be described.

As shown in FIG. 12, vertically aligned areas of row and column conductor strips 326, 330 form a square matrix of square intersecting regions 390. Also, each hole 381 in which is located a piezoresistive bung 342 penetrates each of four row-column conductor strip intersections to form therein four concentric notches, each of which has the shape of a circular arc segment that has a circumferential length of slightly less than 180 degrees. Thus, as shown in FIG. 14A a hole 381 forms in a pair of adjacent row conductor strips 326-1, 326-2 a pair of transversely spaced apart, generally semi-circularly shaped mirror symmetric notches 391, 392 which protrude rearwardly and forwardly, respectively, from front and rear edges 393, 394 of the column conductor strips, the notches being congruent with the perimeter of hole 381.

Figure 14A:
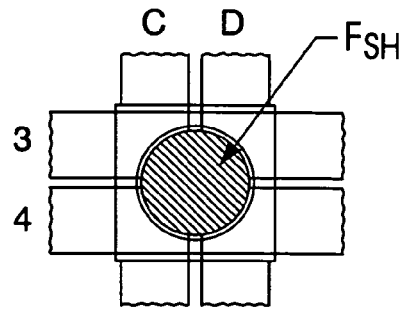
FIG. 14A is a diagrammatic upper plan view of a single shear sensor element of the array of FIGS. 12 and 13.

Similarly, as shown in FIG. 14A, hole 381 forms in a pair of adjacent column conductor strips 330-A, 330-B a pair of longitudinally spaced apart, generally semi-circularly shaped mirror symmetric notches 395, 396 which protrude left and right, respectively, from right and left edges 397, 398 of the column conductor strips, the notches also being congruent with the perimeter of hole 381. With this arrangement, movement of center bung 342 diagonally rearwards to the rear left in FIG. 14A causes a rear portion of the piezoresistive bung to conductively contact column conductor strip 330-A and row conductor strip 326-1, thus increasing electrical conductance between those two conductor strips. Similarly, motion of piezoresistive bung 342 in response to a shear force exerted diagonally forwardly towards the right in FIG. 14A results in proportionally larger electrical conductance between column conductor strip 330-B and row conductor strip 326-2. In an exactly analogous fashion, conductance values between column conductor strip 330-A and row conductor strip 326-2 are increased for shear forces exerted forwardly to the left in FIG. 14A, and conductance values between column conductor strip 330-B and row conductor strip 326-1 are increased for shear forces exerted rearwardly and to the right.

Figure 14B:
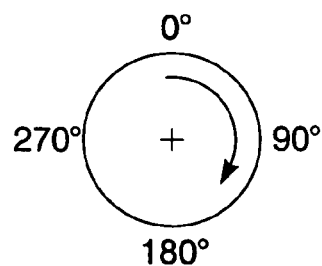
FIG. 14B is a diagrammatic view which defines polar angles of shear forces exerted on the sensor element of FIG. 14A.

Table 1 summarizes hypothetical orders of magnitude variations in resistance between conductor strips of shear sensor 320, for shear forces exerted in directions indicated in FIG. 14B, while Table 2 indicates actual measured values for resistance variation versus shear force exerted along a principal axis of sensitivity of the sensor shown in FIG. 14A.

TABLE 1

Idealized Shear Sensor Resistance vs. Azimuth Angle Direction of Applied 100-gram Shear Force, Fsh

| Azimuth Angle | C-3 | C-4 | D-3 | D-4 |
| --- | --- | --- | --- | --- |
| 0 | 1 KΩ | OC | 1 KΩ | 0 |
| 45° | 10 KΩ | | 100 Ω | 10 KΩ |
| 90° | OC | OC | 1 KΩ | 1 KΩ |
| 135° | OC | 10 KΩ | 10 KΩ | 100 Ω |
| 180° | OC | 1 KΩ | OC | 1 KΩ |
| 225° | 10 KΩ | 100 Ω | OC | 10 KΩ |
| 270° | 1 KΩ | 1 KΩ | OC | OC |

Note:
OC = Open Circuit

TABLE 2

Measured Shear Sensor Resistance vs. Force in Direction of Principal Axis of Sensor Sensitivity

| Grams | Ohms |
| --- | --- |
| 0 | Infinity |
| 100 | 20K |
| 200 | 2K |
| 300 | 1.5K |

Figure 15:
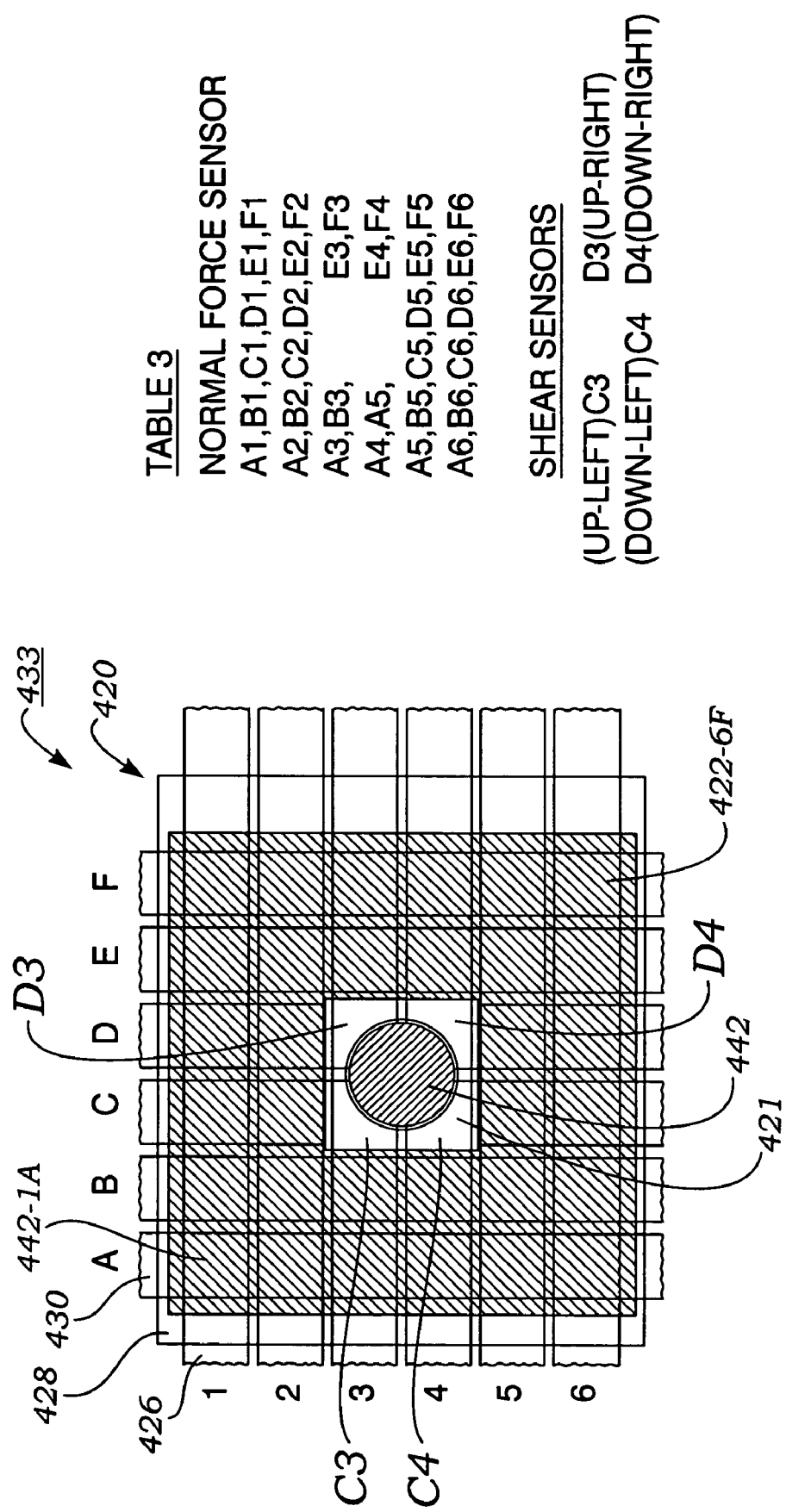
FIG. 15 is a diagrammatic upper plan view of another embodiment of a normal force gradient/shear force sensor array according to the present invention, which utilizes shear sensors having four quadrant electrodes and peripheral normal force sensors.
Figure 16:
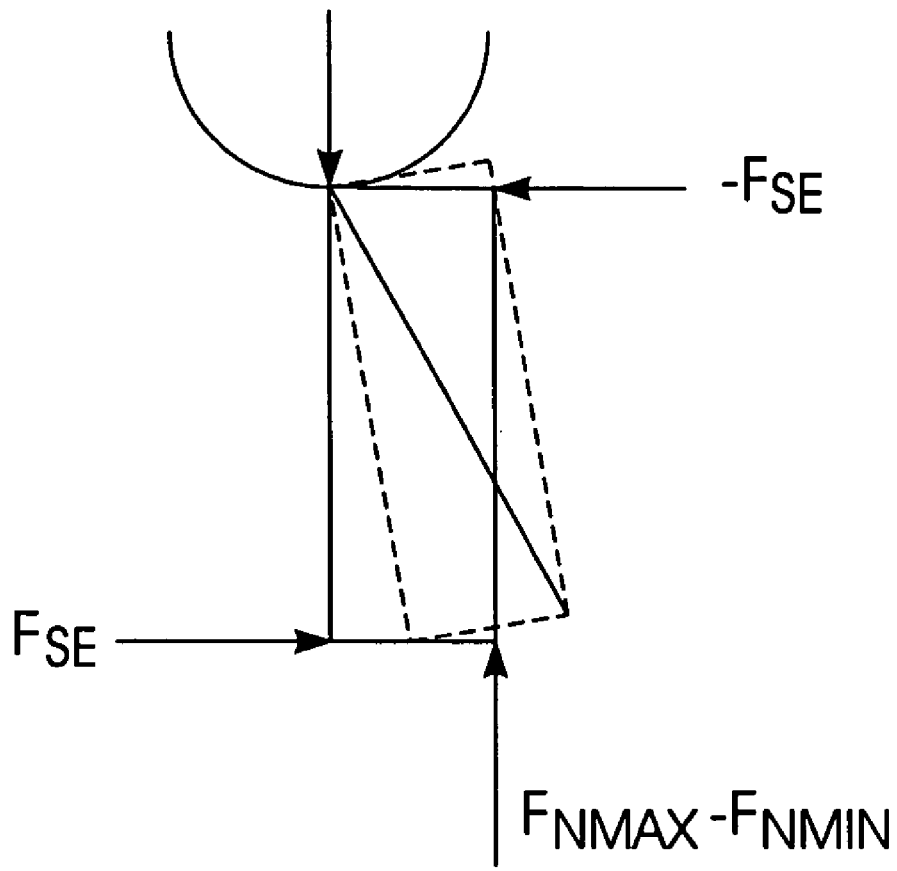
FIG. 16 is a vector diagram which illustrates geometrical relationships between individual forces used to calculate resulting internal shear forces according to the present invention.

FIG. 15 illustrates another embodiment 433 of a normal force gradient/shear force sensor array according to the present invention. Sensory array 433 includes sensor units 420 which each have row conductor strips 426, column conductor strips 430, and a piezoresistive sheet 428 sandwiched therebetween, which are analogous in structure and function to corresponding elements 26, 30, and 28 of peripheral normal force sensor elements 22 of sensor unit 20 depicted in FIGS. 1 and 2 and described above.

Modified sensor array 433 includes a plurality of shear force sensors 421, one of which is shown in FIG. 15, in the place of a square array of four normal force sensors 422. Shear force sensor 421 is substantially identical in structure and function to modified shear force sensor 321 described above. Thus, each shear force sensor 421 of an array of similar shear force sensors has four quadrant sensing electrodes which are formed by notches having the shape of circular arc segments. As shown in FIG. 15, vertically aligned areas of row and column conductor strips 426, 430 form a square matrix of intersecting regions 490. A circular hole 481 through row and column conductor strips 426, 430 intersects each of four adjacent row-column conductor strip intersections to form in the edges of the conductor strips four concentric notches, each of which has the shape of a circular arc segment that has a circumferential length of slightly less than 180 degrees.

As may be understood by referring to FIG. 14A and FIG. 15, hole 481 forms in a pair of row conductor strips 426-3, 426-4 a pair of transversely spaced apart, generally semi-circularly shaped symmetric notches 491, 492 which protrude rearwardly and forwardly, respectively, from front and rear edges 493, 494 of the column conductor strips, the notches being congruent with the perimeter of hole 481. As is also shown in FIG. 15, hole 481 also forms in a pair of adjacent column conductor strips 430-C, 430-D a pair of longitudinally spaced apart, generally semi-circularly shaped mirror symmetric notches 495, 496 which protrude left and right, respectively, from right and left edges 497, 498 of the column conductor strips, the notches also being congruent with the perimeter of hole 481. With this arrangement, movement of center bung 442 diagonally rearwards to the left in FIG. 15 causes a rear portion of the piezoresistive bung to conductively contact column conductor strip 430-C and row conductor strip 426-3, thus increasing electrical conductance between those two conductor strips. Similarly, motion of piezoresistive bung 492 in response to a shear force exerted diagonally forwardly towards the right in FIG. 15 results in proportionally larger electrical conductance between column conductor strip 430-D and row conductor strip 426-4. In an exactly analogous fashion, conductance values between column conductor strip 430-C and row conductor strip 426-4 are increased for shear forces exerted forwardly to the left in FIG. 15, and conductance values between column conductor strip 430-D and row conductor strip 426-3 are increased for shear forces exerted rearwardly and to the right.

As shown in FIG. 15, modified normal force gradient/shear sensor array 433 includes square rings of peripheral normal force sensors 422 which are spaced apart at different radial distances from the center of each shear force sensor 421, thus enabling measurement of normal force gradients in radially spaced apart directions from a shear force sensor. Each peripheral normal force sensor 422 is comprised of an area of piezoresistive sheet material 428 located between intersections of row and column electrode strips 426, 430 not occupied by a shear force sensor 421. Thus, as shown in FIG. 15, a "first-rank" square annular ring of peripheral normal force sensors 422 immediately adjacent to a centrally located shear force sensor 421 includes 12 square plan-view peripheral normal force sensors which are labeled by the corresponding intersections of row and column conductor strips as 422-2B, 422-2C, 422-2D, 422-2E, 422-3E, 422-4E, 422-5E, 422-5D, 422-5C, 422-5B, 4224B, 422-3B. Similarly, there is a "second rank" annular ring of 20 peripheral normal force sensors 422, spaced further from central shear force sensor 421, which circumscribe the first ring. The second rank consists of normal force sensors 422-1A, 422-1B, 422-1C, 422-1D, 422-1E, 422-1F, 422-2F, 422-3F, 422-4F, 422-5F, 422-6F, 422-6E, 422-6D, 422-6C, 422-6B, 422-4A, 422-5A, 422-4A, 422-3A, 422-2A. As will be described in detail below, gradients of normal force sensors in directions radially spaced apart from a central shear force sensor 421 of array 433 are determined by subtracting normal force measurements made by second rank normal force sensors 422 from measurements made by radially adjacent first-rank normal force sensors. For example, the component of a normal force gradient in a diagonal direction rearwardly and to the left in FIG. 15 is determined by subtracting the normal force measurement value of normal force sensors 422-1A from the normal force value measured by sensor 422-2B. Table 3 summarizes the location in array 433 of electrodes for a shear force sensor 421, and of peripheral normal force sensors 422.

TABLE 3

Shear and Normal Sensor Locations For Sensor Array 433 of FIG. 15

| Normal Force Sensors | | | | | |
|---|---|---|---|---|---|
| A1 | B1 | C1 | D1 | E1 | F1 |
| A2 | B2 | C2 | D2 | E2 | F2 |
| A3 | B3 |    |    | E3 | F3 |
| A4 | B4 |    |    | E4 | F4 |
| A5 | B5 | C5 | D5 | E5 | F5 |
| A6 | B6 | C6 | D6 | E6 | F6 |

Shear Sensors (Up-left) C3   (Up-right) D3
(Down-left)    (Down right)
    C4             D4

An algorithm according to the present invention to determine the approximate magnitude and direction of internal shear forces from shear and normal force gradient measurements using an array 33 according to the present invention may be best understood by referring to FIGS. 3A, 3B, 8A, 8B and 16.

Figure 3A:
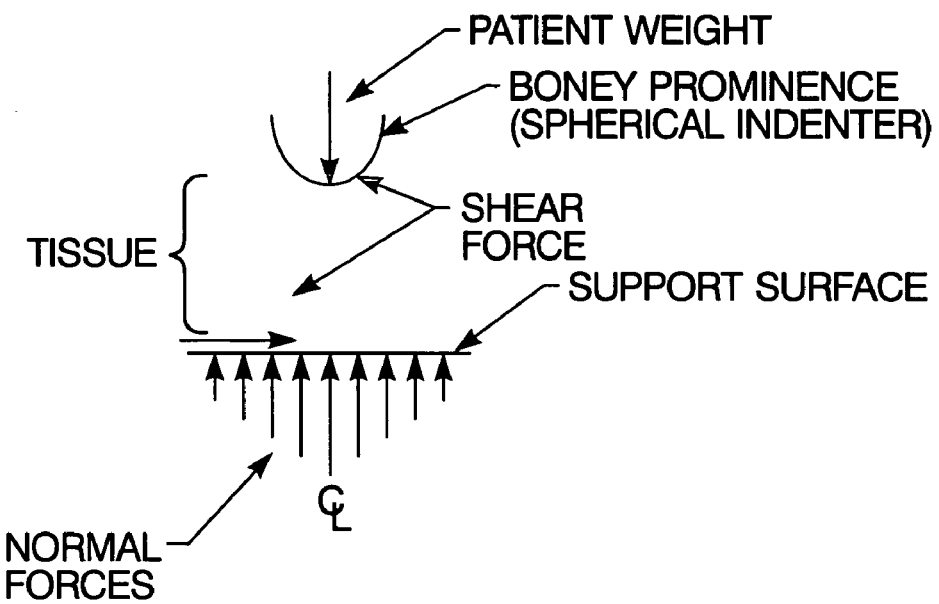
FIG. 3A is a diagrammatic vertical sectional view showing forces exerted by a bony prominence on a shear force sensor according to the present invention, with the shear sensor placed on a support surface such as a bed or chair.

Consider the simple case of a spherical indenter. Referring to FIG. 3A, it can be seen that the moment created by the forces applied by the bone, through the tissue, to the support surface, are additive to the moment introduced by the shear force on the left side of the centerline, but, are reduced by the shear force on the right side. Tissue stress can be inferred from the combination of the moments. The sum of the moments for both internal and external forces is zero and therefore we can infer the internal shear stress from the externally measured shear and normal forces by assuming an internal shape and the internal shape of the bony prominence can be approximated from the spatial force gradient.

Figure 3B:
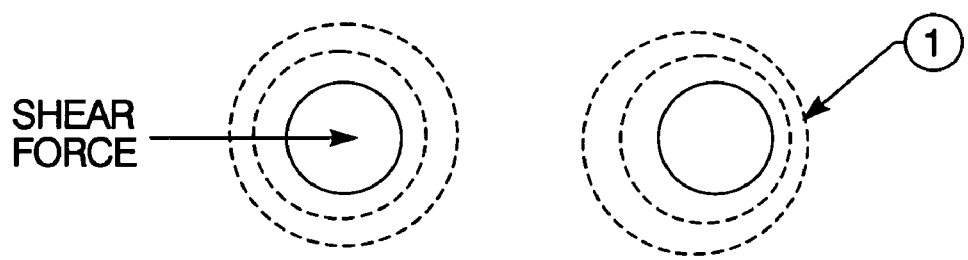
FIG. 3B is a diagrammatic plan view of forces in FIG. 3A.

Referring to FIG. 3B, it can be seen that the displacement of the indenter causes the compression and internal shear strain in the direction of movement. This strain is additive to any externally applied shear forces if they coincide with this direction and subtractive if in an opposing direction.

Definitions:
 Normal Force—force perpendicular to the surface being tested.
 Shear Force—force perpendicular to the normal force.
 Moment—the force multiplied by the distance to the item being influenced.

Given the following external measurements (ref. FIGS. 3A, 3B, 8A and 8B)
 One normal force measured at the center of the shear sensors Fa,
 8 normal force measurements (F) surrounding the shear sensor at a radial distance R, Fb, Fc, Fd, Fe, Ff, Fg, Fh, & Fi
 3 shear force (F) measurements (120 degrees apart) centered Fj, Fk, & Fl
 An indenter of radius R some vertical distance Z from the sensors The externally measured shear and normal forces are assumed to originate from the indenter.

Center the sensor array such that Fa equals the maximum measured normal force $F_{Nmax}$ and is at the center of the shear sensor.

The externally measured shear force ($F_{se}$) is the vector sum of the three measured forces $F_{js}$ $F_{ks}$ $F_{ls}$.

Calculate the vector sum of the differences between the central normal force ($F_{Nmax}$) and the lower surrounding normal forces. In this case there are 8 directions radially outward from the central highest force $F_{Nmax}$. The 8 measured lower forces $F_{bs}$ $F_{cs}$ $F_{ds}$ $F_{es}$ $F_{fs}$ $F_{gs}$ $F_{gs}$ $F_{hs}$ & $F_i$ are R inches from the central $F_{Nmax}$ where each individual vector is its associated radial direction times the difference between that force and $F_{Nmax}$. Call this resultant force $F_{nr}$. This is the normal force gradient vector. The magnitude and direction of the internal shear force is the vector sum of the externally measured shear force $F_{se}$ as established in 2 and normal force gradient vector $F_{nr}$ of 3.

The direction of the internal shear force does not change with values Z. For clinical reasons and to establish the maximum possible internal shear we assume a worst case scenario where Z is minimal.

Since the external shear force is assumed to have originated from the internal indenter, the horizontal component of the internal shear force is assumed to be equal and opposite to the measured external shear.

The force $F_{Nr}$ is assumed to act perpendicular to the surface and at a location y, where y is determined by the magnitude of the vector found in 3.

Internal shear $F_{si}$ is vector sum of 6 (acting along the skin) and 7 (acting perpendicular to the skin).

Following is a sample calculation of internal shear forces exerted on a body part, e.g., a bony prominence of a patient located below a portion of the body part, e.g., overlying tissue supported on a shear/normal force sensor device according to the present invention, with the sensor device in turn supported on a table, bed, chair, or the like.

Referring to FIGS. 1, 10 and 11, shear force sensor resistances Rj, Rk, Rl, are measured between center bung 42 and peripheral electrodes 49, 50 and 51, respectively. Eight normal force sensor resistances Rb, Rc, Rd, Re, Rf, Rg, Rh, and Ri, of the first rank or nearest neighbor normal force sensor elements spaced equidistant from the center of center bung 42, are also measured.

The resistance due to forced contact between the center bung 42 and central normal force sensor 23 is proportional to the normal force at the center of the shear sensor. The external normal force gradient is found by taking a linear slope of the spatial rate of change of normal forces between each of the eight normal forces surrounding the central normal force sensor. The external shear force is found by calculating the vector sum of the three shear force readings. The resultant maximum possible internal shear force is calculated as the vector sum of the spatial normal force gradient and the resultant shear force.

Sample Calculation

Given:

3 resistances due to forced contact between center bung 11b and shear elements 6a, 6b and 6c $R_j=0 \therefore F_j=0$ $R_k=\Delta \therefore F_k=0$ $R_L=2K\Omega \therefore F_i=200$ grams=0.44 lb 8 resistances due to forced contact between normal force conductive strips 7 and 9 through semi-conductor 11a.

$R_b=2K\Omega \therefore F_b=0.44$ lb $R_c=1.5K\Omega \therefore F_c=0.66$ lb $R_d=100 \Omega \therefore F_d=1$ lb $R_e=1.5K\Omega \therefore F_e=0.66$ lb $R_f=2K\Omega \therefore F_f=0.44$ lb $R_g=20K\Omega \therefore F_g=0.02$ lb $R_h=200K\Omega \therefore F_h=0.002$ lb $R_i=20K\Omega \therefore F_i=0.02$ lb 1 resistance due to forced contact between center bung 11b and strip 12

$R_n max=100 \Omega \therefore F_n max=1$ lb

Distance between center and normal force elements:

1 in. Orthogonally to b, d, f, h 1.4 in diagonally to c, e, g, l

Calculating the normal force gradient ($\Delta$)

$F_n max \cdot F_b,d,f,h \times r$ plus $F_n max \cdot F_c, e, g, l \times 1.4r$ Gives $F\Delta$. 0.8 lb @ location d Calculating the external shear force gives $F_{se}=F_m \cdot F_k \cdot F_l=0.44$ lb in direction f Calculating the internal shear force as the vector sum of gradient $\Delta$ and external shear $F\Delta Xr + F_{se} = (0.8)(1) + 0.44 = 1.84$ lb.

Internal shear forces calculated in the foregoing manner may be somewhat higher than actual internal shear forces. However, for purposes of monitoring potential injuries to high risk patients, it is preferable to use the maximum calculated values of internal shear forces and stresses, in a "worst-case" or most conservative evaluation of damage potential for a patient. Thus, for situations in which a human body supported by a surface is not moving and when external forces exerted on the body by the surface are not cushioned by a thick layer of intervening muscle tissue, it is assumed that maximum values of shear forces calculated from a combination of external shear forces and normal force gradients as described above, result in equal and opposite shear stress-causing shear forces being exerted by an internal anatomical feature such as a bony prominence on internal tissue.

Figure 8A:
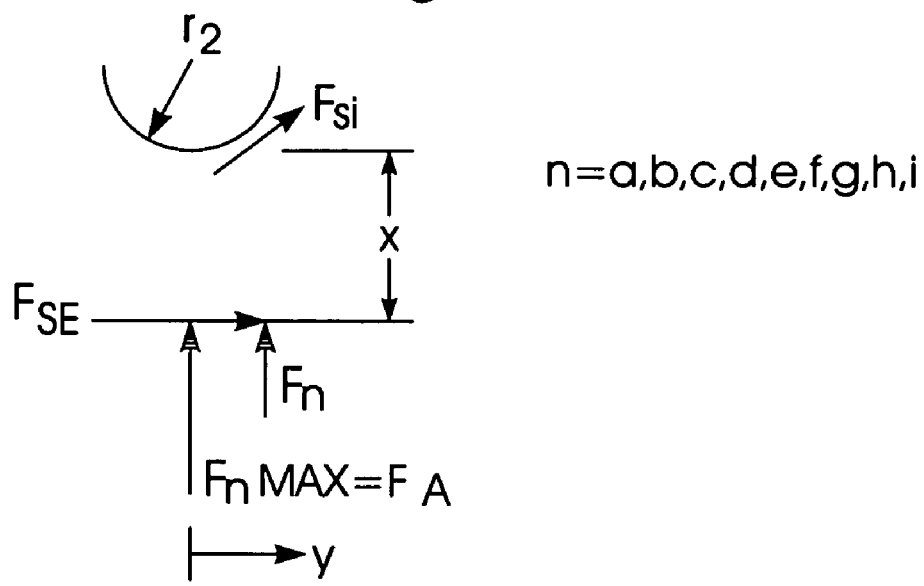
FIG. 8A is a vector diagram of forces exerted by an object on a shear force sensor according to the present invention, as viewed in a vertical sectional plane similar to that of FIG. 3A.
Figure 8B:
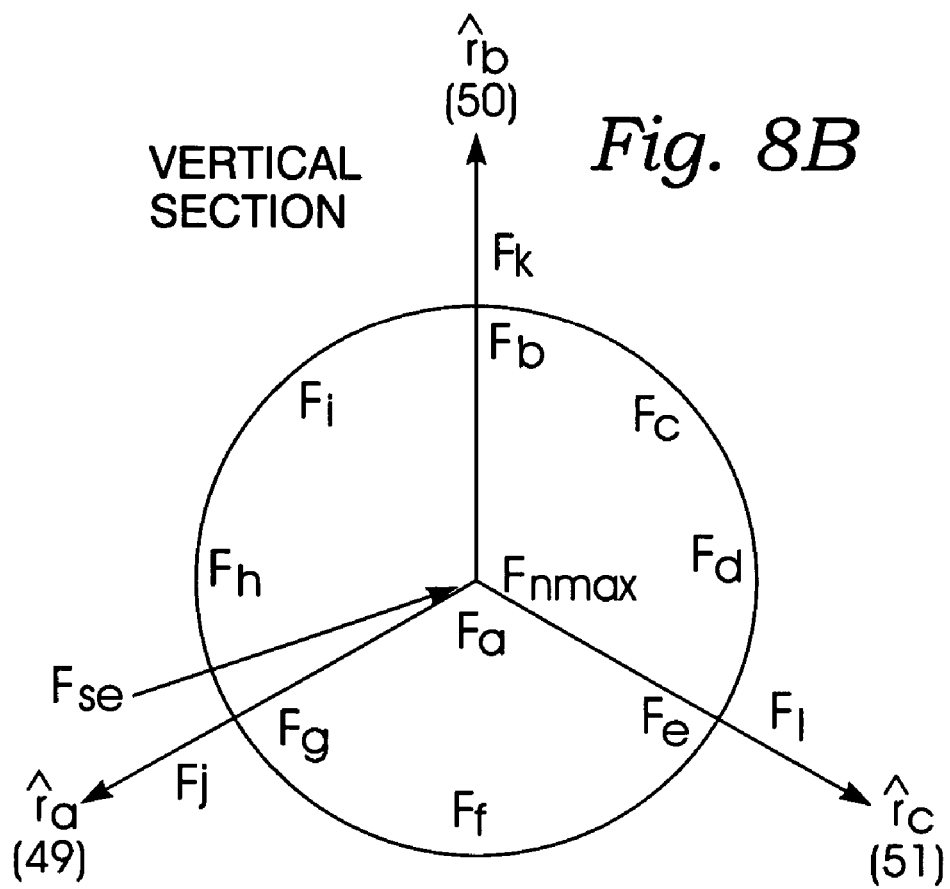
FIG. 8B is a plan view showing the relationship of measurements of shear force, central normal force, and peripheral normal forces used to determine shear force, normal force gradient, and internal shear force using the apparatus and method of the present invention.
Figure 8C:
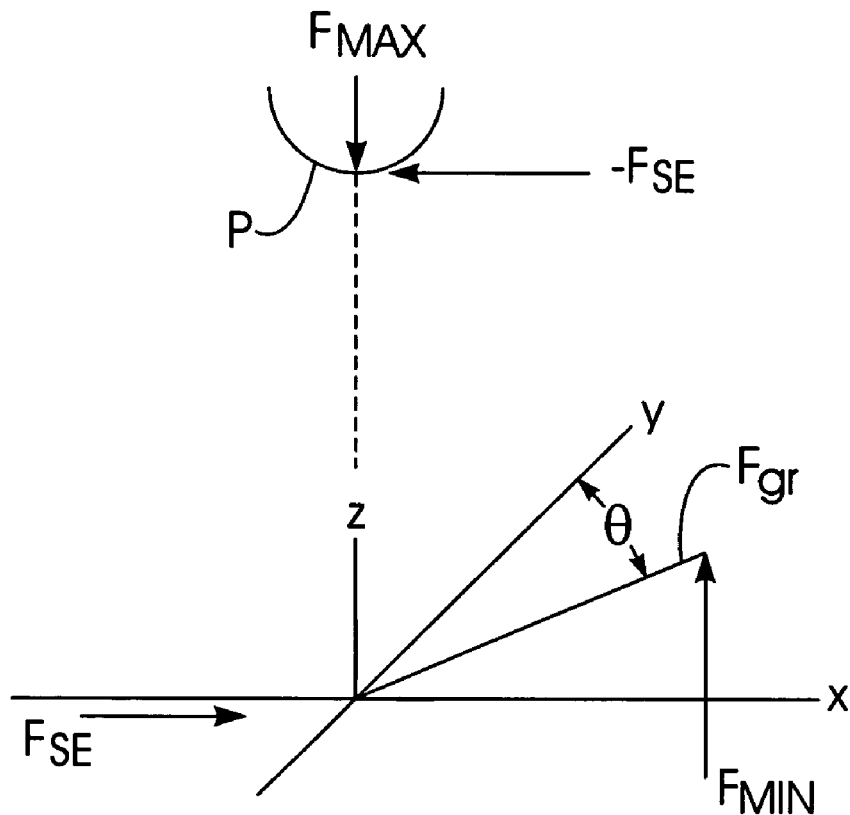
FIG. 8C is a diagrammatic view showing how maximum internal tissue stress forces are calculated from external shear force and normal force gradient measurements.
Figure 9:
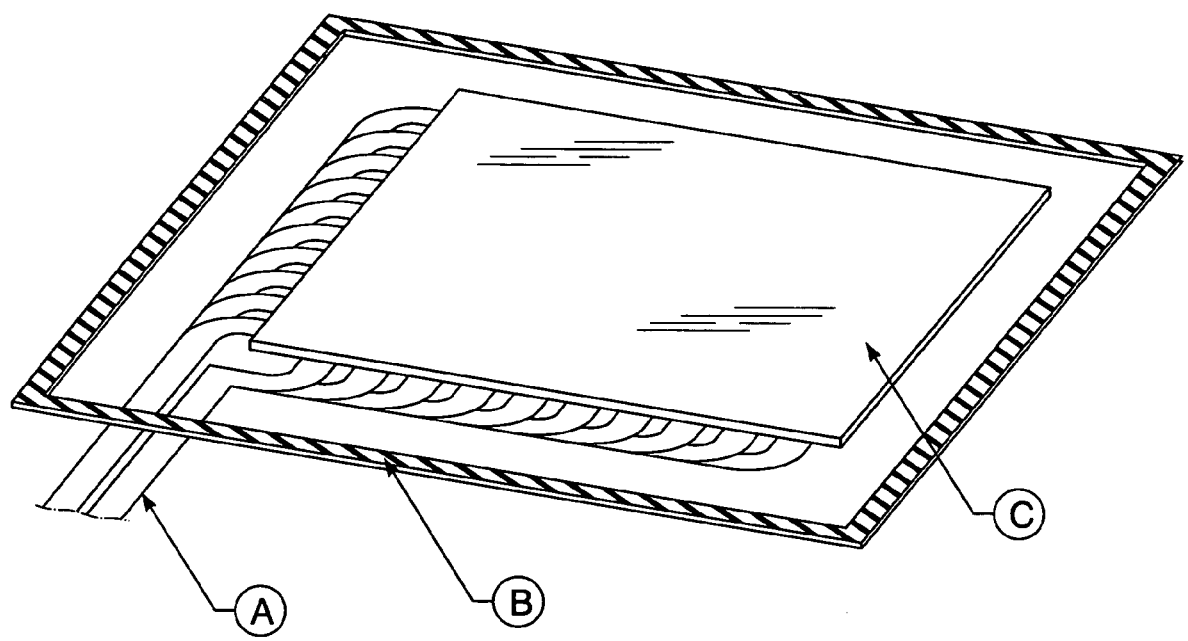
FIG. 9 is an upper perspective view of an array of normal force gradient/shear force sensors according to the present invention.

FIG. 8C is a diagrammatic view showing how maximum internal tissue stresses are calculated from external shear force and normal force gradient measurements according to the present invention. As shown in FIG. 8C, the maximum internal shear force on a tissue located for example, at a bony prominence P is given by the equation:

$$S=F_{SE}*\sin\Theta \cdot i + F_{se}*\cos\Theta \cdot j + F_{GR} \cdot k, \text{ wherein:}$$

S=Total Maximum Internal Shear Stress $F_{SE}$=Measured External Shear Force Vector $\Theta$=angle from $F_{MAX}$ and the maximum force gradient in an X-Y plane $F_{GR}=F_{MAX}-F_{MIN}$ $S=F_{SE}*\sin\Theta \cdot i + F_{SE}*\cos\Theta \cdot j + F_{GR} \cdot k$ $F_{MAX}$=Maximum Measured Normal Force $F_{MIN}$=Minimum Measured Normal Force $F_{MAX}-F_{MIN}$=Force Gradient Vector

What is claimed is:

1. A shear force sensing transducer for measuring tangential shear forces exerted parallel to a surface, said transducer comprising;
   a. a first, lower cover sheet made of a thin sheet of flexible material,
   b. an electrode assembly comprising an insulating substrate sheet having upper and lower surfaces, a plurality of circumferentially spaced apart, electrically isolated planar electrodes affixed to at least one of said upper and lower surfaces, said electrodes radiating from a common center of a circular bore disposed perpendicularly through thickness dimensions of said electrodes and said electrode and said substrate sheet, said bore being coaxial with said common center of said electrodes, said electrodes having inner conductive edges adjacent to said bore,
   c. an electrically conductive body located with said bore,
   d. a second, upper cover sheet made of a thin sheet of flexible material, and
   e. means for coupling relative parallel motion of said lower and upper cover sheets to said electrode assembly and said body in response to a shear force exerted on said transducer to thereby cause radial contacting motion between said body and said conductive edges of said electrode and thereby causing electrical conductance between said body and said electrodes to vary in a predetermined manner with the magnitude and direction of said shear force.

2. The transducer of claim 1 wherein at least one of said body and each of said electrodes is further defined as being made of a piezoresistive material.

3. The transducer of claim 1 wherein said body is further defined as having an outer perimeter which has a shape similar to an inner cylindrical surface of said hole.

4. The transducer of claim 1 wherein said inner conductive edges of said electrodes are further defined as being circular arc segments.

5. The transducer of claim 4 wherein said plurality of electrodes is further defined as comprising three electrodes.

6. The transducer of claim 5 wherein said inner conductive edges of said electrodes are spaced circumferentially apart at equal circumferential intervals.

7. The transducer of claim 6 wherein said body is further defined as having in plan view a circular disk shape.

8. The transducer of claim 4 wherein said plurality of electrodes is further defined as comprising four electrodes.

9. The transducer of claim 8 wherein said inner conductive edges of said electrodes are spaced circumferentially apart at equal circumferential intervals.

10. The transducer of claim 9 wherein said body is further defined as having a circular disk shape.

11. A normal force gradient/shear force sensing transducer device for measuring in directions radially spaced from said shear force sensing transducer of claim 1, gradients of normal forces exerted perpendicular to a surface, said device comprising in combination;
    a. said shear force sensing transducer of claim 1,
    b. a plurality of at least two normal force sensing transducers, at least one of which is spaced radially from said electrically conductive body of said shear force sensing transducer, and
    c. means for determining a difference between normal force values sensed by said normal force sensing transducer.

12. The device of claim 11 wherein said plurality of normal force sensing transducer comprises at least one first rank normal force sensing transducer located on a first perimeter line which encloses said body, and at least one second rank normal force sensing transducer located on a second perimeter line which encloses said body, said second rank perimeter line being spaced radially apart from said first perimeter line.

13. The device of claim 11 wherein at least one of said normal force sensing transducers is a central normal force sensing transducer which is perpendicularly aligned with said body of said shear force sensing transducer.

14. The device of claim 13 wherein at least one of said two force sensing transducers is a peripheral normal force sensing transducer spaced radially outward from said first central normal force sensing transducer.

15. The device of claim 14 further including at least a second peripheral normal force sensing transducer spaced radially from said first peripheral normal force sensing transducer.

16. The device of claim 13 wherein said plurality of normal force sensing transducers includes at least one first rank normal force sensing transducer located on a first perimeter line which encloses said body.

17. The device of claim 16 wherein said plurality of normal force sensing transducers includes at least one second rank normal force sensing transducer located on a second perimeter line which encloses said body, said second rank perimeter line being spaced radially apart from said first perimeter line.

18. A shear force sensor array comprising a plurality of spaced apart shear force sensors of claim 1, said plurality of shear force sensors being arranged in a two-dimensional matrix.

19. The shear force sensor array of claim 18 wherein said means for making electrically conductive contact to said electrodes is further defined as being a plurality of electrode lead-out conductor strips.

20. The shear force sensor array of claim 19 wherein said means for making electrically conductive contact with said body is further defined as being a body lead-out conductor strip.

* * * * *